(12) United States Patent
Young et al.

(10) Patent No.: US 7,074,913 B2
(45) Date of Patent: Jul. 11, 2006

(54) **RECEPTOR FOR *B ANTHRACIS* TOXIN**

(75) Inventors: John A. T. Young, Madison, WI (US); Kenneth A Bradley, Madison, WI (US); R. John Collier, Wellesley, MA (US); Jeremy S. Mogridge, Toronto (CA)

(73) Assignees: Wisconsin Alumni Research Foundation, Madison, WI (US); President and Fellows of Harvard College, Cambridge, MA (US)

( * ) Notice: Subject to any disclaimer, the term of this patent is extended or adjusted under 35 U.S.C. 154(b) by 492 days.

(21) Appl. No.: 09/970,076

(22) Filed: Oct. 3, 2001

(65) Prior Publication Data

US 2006/0110801 A1  May 25, 2006

Related U.S. Application Data

(60) Provisional application No. 60/251,481, filed on Dec. 5, 2000.

(51) Int. Cl.
  *C07H 21/04* (2006.01)
  *C07H 21/02* (2006.01)
  *C12N 1/12* (2006.01)
  *C12N 15/00* (2006.01)
  *C12N 15/74* (2006.01)
  *C12N 15/63* (2006.01)
  *C12P 21/04* (2006.01)

(52) U.S. Cl. ............... 536/23.7; 536/23.1; 536/23.4; 435/320.1; 435/252.1; 435/69.3; 435/71.1

(58) Field of Classification Search ............. 530/23.1, 530/23.4, 23.7; 435/320.1, 252.3, 69.3, 252.1
See application file for complete search history.

(56) References Cited

U.S. PATENT DOCUMENTS

| | | | |
|---|---|---|---|
| 5,591,631 A * | 1/1997 | Leppla et al. | |
| 5,677,274 A * | 10/1997 | Leppla et al. | |
| 6,022,855 A * | 2/2000 | Thomas et al. | |
| 6,329,156 B1 * | 12/2001 | Cirino et al. | 435/7.21 |
| 6,485,925 B1 * | 11/2002 | Duesbery et al. | 435/23 |
| 6,569,662 B1 | 5/2003 | Tang et al. | 435/212 |
| 6,592,872 B1 | 7/2003 | Klimpel et al. | 424/197.11 |
| 2002/0039588 A1 * | 4/2002 | Collier et al. | 424/246.1 |
| 2002/0048590 A1 * | 4/2002 | Klimpel et al. | 424/246.1 |
| 2002/0051791 A1 * | 5/2002 | Galloway et al. | 424/190.1 |
| 2002/0142002 A1 * | 10/2002 | Galloway et al. | 424/184.1 |
| 2002/0197272 A1 * | 12/2002 | Galloway et al. | 424/190.1 |
| 2003/0003109 A1 * | 1/2003 | Galloway et al. | 424/190.1 |
| 2003/0096333 A1 * | 5/2003 | Duesbery et al. | 435/15 |
| 2003/0108556 A1 * | 6/2003 | Mekalanos et al. | 424/184.1 |
| 2003/0119720 A1 * | 6/2003 | Khan et al. | 514/2 |
| 2003/0198651 A1 * | 10/2003 | Klimpel et al. | 424/246.1 |
| 2003/0202989 A1 * | 10/2003 | Collier et al. | 424/236.1 |
| 2005/0196407 A1 * | 9/2005 | Young et al. | 424/190.1 |

FOREIGN PATENT DOCUMENTS

| | | |
|---|---|---|
| WO | WO 00/39284 | 7/2000 |
| WO | WO 01/34626 | 5/2001 |
| WO | WO 01/53312 | 7/2001 |
| WO | WO 01/77137 | 10/2001 |
| WO | WO 02/10217 | 2/2002 |
| WO | WO 02/46228 A2 * | 6/2002 |

OTHER PUBLICATIONS

Pannifer et al Nature, 414:229-233 Nov. 8, 2001.*
Bradley et al Nature, 414:255-228 Nov. 8, 2001.*
Benson et al, Biochemistry 37:3941-48; 1998.*
Elliott et al, Biochemistry, 39:6706-6713; 2000.*
Cunningham et al, PNAS 99/10: 7049-53, 2002.*
Kumar et al, Infection & Immunity 69/10:6532-36, 2001.*
Chauhan et al, Infection & Immunity 70/8:4477-84, 2002.*
Mogridge et al, J. Bacteriology 183/6:2111-116, 2001.*
St. Croix et al, Science, 289:1197-1202, 2000.*
NCBI; GenBank Accession# BC012074, 2001.*
Accession# AF421380, 2001.*
Accession# AF279145, 2001.*
Accession# AAD05303, 2001.*
Batra et al, BBRC 281:186-192, 2001.*
Zhao et al, JBC, 270/31:18626-630, 1995.*

(Continued)

*Primary Examiner*—N. M. Minnifield
(74) *Attorney, Agent, or Firm*—Quarles &Brady LLP

(57) ABSTRACT

The present invention relates to mammalian anthrax toxin receptor polypeptides and polynucleotides encoding same as well as related polypeptides and polynucleotides, vectors containing the polynucleotides and polypeptides, host cells containing related polynucleotide molecules, and cells displaying no anthrax toxin receptor on an exterior surface of the cells-minus cell lines and animals. The present invention also relates to methods for identifying molecules that bind the anthrax toxin receptor and molecules that reduce the toxicity of anthrax toxin. Finally, the present invention provides methods for treating human and non-human animals suffering from anthrax.

14 Claims, 1 Drawing Sheet

OTHER PUBLICATIONS

Milne et al, Mol. Microbiol. 15/4:661-666, 1995.*
Mourez et al, Trends in Microbiology 10/6:287-93, 2002.*
Brossier et al, Toxicon, 2001; 39:1747-1755.*
Chaudry et al, TRENDS in Microbiology, Feb. 2002, 10/2:58-62.*
Moayeri et al, Current Opinion in Microbiology, 2004, 7:19-24.*
Abrami et al, TRENDS in Microbiology, Feb. 2005, 13/2:72-78.*
Laird et al, Proetin Expression and Purification, 2004, 38:145-152.*
Mourez et al, TRENDS in Microbiology, Jun. 2002, 10/6:287-293.*
Bradley et al, Biochemical Pharmacology, 2003, 65:309-314.*
Lacey et al, Current Topics Microbiol. Immunol., 2002, 271:61-85.*
Beauregard, et al., "Anthrax Toxin Entry into Polarized Epithelial Cells," *Infection and Immunity* 67:3026-3030 (1999).
Boerger, et al., "Retroviral vectors preloaded with a viral receptor-ligand bridge protein are targeted to specific cell types," *Proc. Natl. Acad. Sci. USA* 96:9867-9872 (1999).
Dickeson, et al., "Ligand recognition by the I domain-containing integrins," *CMLS Cell. Mol. Life Sci.* 54:556-566 (1998).
Elliott, Jennifer, "Assembly and Translocation of Anthrax Toxin," Ph.D. Thesis, Department of Microbiology (Cambridge, MA, Harvard University) pp. 35-65 (1998).
Escuyer, et al., "Anthrax Protective Antigen Interacts with a Specific Receptor on the Surface of CHO-K1 Cells," *Infection and Immunity* 59:3381-3386 (1991).
Genbank Accession No. AK001463, "Homo sapiens cDNA FLJ10601 fis, clone NT2RP2005000," *NCBI Sequence Viewer* 2 pages (Sep. 28, 2001).
Genbank Accession No. BC012074, "Homo sapiens, similar to tumor endothelial marker 8, clone MGC:19967 IMAGE:4563020, mRNA, complete cds," *NCBI Sequence Viewer* 2 pages (Sep. 25, 2001).
Genbank Accession No. NM_032208, "Homo sapiens tumor endothelial marker 8 (TEM8), mRNA," *NCBI Sequence Viewer* 3 pages (Nov. 2, 2001).
Gordon, et al., "Inhibitors of Receptor-Mediated Endocytosis Block the Entry of *Bacillus anthracis* Adenylate Cyclase Toxin but Not That of *Bordetella pertussis* Adenylate Cyclase Toxin," *Infection and Immunity* 56:1066-1069 (1988).
Hanna, et al., "On the role of macrophages in anthrax," *Proc. Natl. Acad. Sci. USA* 90:10198-10201 (1993).
Hanna, P., "Anthrax Pathogenesis and Host Response,"*Current Topics in Microbiology and Immunology* 225:13-35 (1998).
Klimpel, et al., "Anthrax toxin protective antigen is activated by a cell surface protease with the sequence specificity and catalytic properties of furin," *Proc. Natl. Acad. Sci. USA* 89:10277-10281 (1992).

Lee, et al., "Crystal Structure of the A Domain from the α Subunit of Integrin CR3 (CD11b/CD18)," *Cell* 80:631-638 (1995).
Leppla, Stephan A., "The bifactorial *Bacillus anthracis* lethal and oedema toxins," *The Comprehenisiv Sourcebook of Bacterial Protein Toxins* Chapter 12:243-263 (1999).
Menard, et al., "The Vacuolar ATPase proton pump is required for the cytotoxicity of *Bacillus anthracis* lethal toxin," *FEBS Letters* 386:161-164 (1996).
Miller, et al., "Anthrax Protective Antigen: Prepore-to-Pore Conversion," *Biochemistry* 38:10432-10441 (1999).
Milne, et al., "Anthrax Protective Antigen Forms Oligomers during Intoxication of Mammalian Cells," *The Journal of Biological Chemistry* 269:20607-20612 (1994).
Petosa, et al., "Crystal structure of the anthrax toxin protective antigen," *Letters to Nature* 385:833-838 (1997).
Snitkovsky et al, "Cell-specific viral targeting mediated by a soluble retroviral receptor-ligand fusion protein," *Proc. Natl. Acad. Sci. USA* 96:7063-7068 (1998).
Snitkovsky, et al., "A TVA-Single-Chain Antibody Fusion Protein Mediates Specific Targeting of a Subgroup A Avian Leukosis Virus Vector to Cells Expressing a Tumor-Specific Form of Epidermal Growth Factor Receptor," *Journal of Virology* 74:9540-9545 (2000).
Snitkovsky, et al, "Targeting Avian Leukosis Virus Subgroup A Vectors by Using a TVA-VEGF Bridge Protein," *Journal of Virology* 75:1571-1575 (2001).
Croix, et al., "Genes Expressed in Human Tumor Endothelium," *Science* 289:1197-1202 (2000).
Zamore, Philip D., "RNA interference: listening to the sound of silence," *Nature Structural Biology* 8:746-750 (2001).
Holtzman, D.A., "Human TANGO 197 Coding Sequence," EMBL Accession #AAA47455 (2000).
Leppla, et al. "Isolation and Characterization of Chinese Hamster Ovary Cell Mutants Lacking the Receptor for Anthrax Toxin Protective Antigen," Bacterial protein Toxins, Zbl. Bakt. Suppl. 28 (1996).
Rosen, et al., "Human Albumin Fusion Protein #549," EMBL Accession #ABG63874 (2002).
Ruben, et al., "Human Gene 4 Encoded Secreted Protein HWLFR02, SEQ ID No.:94," EMBL Accession #AAE01439 (2001).
Ruben, et al., "Human Secreted Protein-Encoding-Encoding Gene 4 cDNA Clone HWLFR02, SEQ ID No.:14," EMBL Accession #AAD05303 (2001).
St. Croix, et al., "Human Tumour Endothelial Marker Polypeptide SEQ IDNO:232," EMBL Accession #ABB90750 (2002).
St. Croix, et al., "Human Tumour Endothelial Marker Polynucleotide SEQ ID No.:231," EMBL Accession #ABL92104 (2002).
Tang, et al., "Human Polypeptide SEQ ID No.:2121," EMBL Accession #AAM38976 (2001).
Tang, et al., "Human Polynucleotide SEQ ID No.:335," EMBL Accession #AAI58132 (2001).

* cited by examiner

SEQUENCE LISTING

```
<160> NUMBER OF SEQ ID NOS: 10

<210> SEQ ID NO 1
<211> LENGTH: 1414
<212> TYPE: DNA
<213> ORGANISM: Homo sapiens
<220> FEATURE:
<221> NAME/KEY: CDS
<222> LOCATION: (104)..(1207)

<400> SEQUENCE: 1
aggacccgcg aggaagggcc cgcggatggc gcgtccctga gggtcgtggc gagttcgcgg      60
agcgtgggaa ggagcggacc ctgctctccc cgggctgcgg gcc atg gcc acg gcg     115
                                                Met Ala Thr Ala
                                                  1 gag cgg aga gcc ctc ggc atc ggc ttc cag tgg ctc tct ttg gcc act     163
Glu Arg Arg Ala Leu Gly Ile Gly Phe Gln Trp Leu Ser Leu Ala Thr
  5                  10                  15                  20 ctg gtg ctc atc tgc gcc ggg caa ggg gga cgc agg gag gat ggg ggt     211
Leu Val Leu Ile Cys Ala Gly Gln Gly Gly Arg Arg Glu Asp Gly Gly
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 25  |     |     |     |     | 30  |     |     |     |     | 35  |     |     |     |      |
| cca | gcc | tgc | tac | ggc | gga | ttt | gac | ctg | tac | ttc | att | ttg | gac | aaa | tca | 259  |
| Pro | Ala | Cys | Tyr | Gly | Gly | Phe | Asp | Leu | Tyr | Phe | Ile | Leu | Asp | Lys | Ser |      |
|     |     |     | 40  |     |     |     | 45  |     |     |     | 50  |     |     |     |     |      |
| gga | agt | gtg | ctg | cac | cac | tgg | aat | gaa | atc | tat | tac | ttt | gtg | gaa | cag | 307  |
| Gly | Ser | Val | Leu | His | His | Trp | Asn | Glu | Ile | Tyr | Tyr | Phe | Val | Glu | Gln |      |
|     |     | 55  |     |     |     |     | 60  |     |     |     |     | 65  |     |     |     |      |
| ttg | gct | cac | aaa | ttc | atc | agc | cca | cag | ttg | aga | atg | tcc | ttt | att | gtt | 355  |
| Leu | Ala | His | Lys | Phe | Ile | Ser | Pro | Gln | Leu | Arg | Met | Ser | Phe | Ile | Val |      |
|     | 70  |     |     |     |     | 75  |     |     |     |     | 80  |     |     |     |     |      |
| ttc | tcc | acc | cga | gga | aca | acc | tta | atg | aaa | ctg | aca | gaa | gac | aga | gaa | 403  |
| Phe | Ser | Thr | Arg | Gly | Thr | Thr | Leu | Met | Lys | Leu | Thr | Glu | Asp | Arg | Glu |      |
| 85  |     |     |     |     | 90  |     |     |     |     | 95  |     |     |     |     | 100 |      |
| caa | atc | cgt | caa | ggc | cta | gaa | gaa | ctc | cag | aaa | gtt | ctg | cca | gga | gga | 451  |
| Gln | Ile | Arg | Gln | Gly | Leu | Glu | Glu | Leu | Gln | Lys | Val | Leu | Pro | Gly | Gly |      |
|     |     |     |     | 105 |     |     |     |     | 110 |     |     |     |     | 115 |     |      |
| gac | act | tac | atg | cat | gaa | gga | ttt | gaa | agg | gcc | agt | gag | cag | att | tat | 499  |
| Asp | Thr | Tyr | Met | His | Glu | Gly | Phe | Glu | Arg | Ala | Ser | Glu | Gln | Ile | Tyr |      |
|     |     |     | 120 |     |     |     | 125 |     |     |     |     | 130 |     |     |     |      |
| tat | gaa | aac | aga | caa | ggg | tac | agg | aca | gcc | agc | gtc | atc | att | gct | ttg | 547  |
| Tyr | Glu | Asn | Arg | Gln | Gly | Tyr | Arg | Thr | Ala | Ser | Val | Ile | Ile | Ala | Leu |      |
|     |     | 135 |     |     |     |     | 140 |     |     |     |     | 145 |     |     |     |      |
| act | gat | gga | gaa | ctc | cat | gaa | gat | ctc | ttt | ttc | tat | tca | gag | agg | gag | 595  |
| Thr | Asp | Gly | Glu | Leu | His | Glu | Asp | Leu | Phe | Phe | Tyr | Ser | Glu | Arg | Glu |      |
|     | 150 |     |     |     |     | 155 |     |     |     |     | 160 |     |     |     |     |      |
| gct | aat | agg | tct | cga | gat | ctt | ggt | gca | att | gtt | tac | tgt | gtt | ggt | gtg | 643  |
| Ala | Asn | Arg | Ser | Arg | Asp | Leu | Gly | Ala | Ile | Val | Tyr | Cys | Val | Gly | Val |      |
| 165 |     |     |     |     | 170 |     |     |     |     | 175 |     |     |     |     | 180 |      |
| aaa | gat | ttc | aat | gag | aca | cag | ctg | gcc | cgg | att | gcg | gac | agt | aag | gat | 691  |
| Lys | Asp | Phe | Asn | Glu | Thr | Gln | Leu | Ala | Arg | Ile | Ala | Asp | Ser | Lys | Asp |      |
|     |     |     |     | 185 |     |     |     |     | 190 |     |     |     |     | 195 |     |      |
| cat | gtg | ttt | ccc | gtg | aat | gac | ggc | ttt | cag | gct | ctg | caa | ggc | atc | atc | 739  |
| His | Val | Phe | Pro | Val | Asn | Asp | Gly | Phe | Gln | Ala | Leu | Gln | Gly | Ile | Ile |      |
|     |     |     | 200 |     |     |     | 205 |     |     |     |     | 210 |     |     |     |      |
| cac | tca | att | ttg | aag | aag | tcc | tgc | atc | gaa | att | cta | gca | gct | gaa | cca | 787  |
| His | Ser | Ile | Leu | Lys | Lys | Ser | Cys | Ile | Glu | Ile | Leu | Ala | Ala | Glu | Pro |      |
|     |     | 215 |     |     |     |     | 220 |     |     |     |     | 225 |     |     |     |      |
| tcc | acc | ata | tgt | gca | gga | gag | tca | ttt | caa | gtt | gtc | gtg | aga | gga | aac | 835  |
| Ser | Thr | Ile | Cys | Ala | Gly | Glu | Ser | Phe | Gln | Val | Val | Val | Arg | Gly | Asn |      |
|     | 230 |     |     |     |     | 235 |     |     |     |     | 240 |     |     |     |     |      |
| ggc | ttc | cga | cat | gcc | cgc | aac | gtg | gac | agg | gtc | ctc | tgc | agc | ttc | aag | 883  |
| Gly | Phe | Arg | His | Ala | Arg | Asn | Val | Asp | Arg | Val | Leu | Cys | Ser | Phe | Lys |      |
| 245 |     |     |     |     | 250 |     |     |     |     | 255 |     |     |     |     | 260 |      |
| atc | aat | gac | tcg | gtc | aca | ctc | aat | gag | aag | ccc | ttt | tct | gtg | gaa | gac | 931  |
| Ile | Asn | Asp | Ser | Val | Thr | Leu | Asn | Glu | Lys | Pro | Phe | Ser | Val | Glu | Asp |      |
|     |     |     |     | 265 |     |     |     |     | 270 |     |     |     |     | 275 |     |      |
| act | tat | tta | ctg | tgt | cca | gcg | cct | atc | tta | aaa | gaa | gtt | ggc | atg | aaa | 979  |
| Thr | Tyr | Leu | Leu | Cys | Pro | Ala | Pro | Ile | Leu | Lys | Glu | Val | Gly | Met | Lys |      |
|     |     |     | 280 |     |     |     | 285 |     |     |     |     | 290 |     |     |     |      |
| gct | gca | ctc | cag | gtc | agc | atg | aac | gat | ggc | ctc | tct | ttt | atc | tcc | agt | 1027 |
| Ala | Ala | Leu | Gln | Val | Ser | Met | Asn | Asp | Gly | Leu | Ser | Phe | Ile | Ser | Ser |      |
|     |     | 295 |     |     |     |     | 300 |     |     |     |     | 305 |     |     |     |      |
| tct | gtc | atc | atc | acc | acc | aca | cac | tgt | tct | gac | ggt | tcc | atc | ctg | gcc | 1075 |
| Ser | Val | Ile | Ile | Thr | Thr | Thr | His | Cys | Ser | Asp | Gly | Ser | Ile | Leu | Ala |      |
|     | 310 |     |     |     |     | 315 |     |     |     |     | 320 |     |     |     |     |      |
| atc | gcc | ctg | ctg | atc | ctg | ttc | ctg | ctc | cta | gcc | ctg | gct | ctc | ctc | tgg | 1123 |
| Ile | Ala | Leu | Leu | Ile | Leu | Phe | Leu | Leu | Leu | Ala | Leu | Ala | Leu | Leu | Trp |      |
| 325 |     |     |     |     | 330 |     |     |     |     | 335 |     |     |     |     | 340 |      |
| tgg | ttc | tgg | ccc | ctc | tgc | tgc | act | gtg | att | atc | aag | gag | gtc | cct | cca | 1171 |

-continued

```
Trp Phe Trp Pro Leu Cys Cys Thr Val Ile Ile Lys Glu Val Pro Pro
            345                 350                 355 ccc cct gcc gag gag agt gag gaa aat aaa ata aaa taacaagaag         1217
Pro Pro Ala Glu Glu Ser Glu Glu Asn Lys Ile Lys
            360                 365 aagaaagaaa gaaatcccac agaaacagat aacctaacac agcccgtgca acgtatttta  1277
tacaatgctc tgaaaatcat agtctcaatc tagacagtct tttcctctag ttccctgtat  1337
tcaaatccca gtgtctaaca ttcaataaat agctatatga aatcaaaaaa aaaaaaaaaa  1397
aaaaaaaaaa aaaaaaa                                                 1414

<210> SEQ ID NO 2
<211> LENGTH: 368
<212> TYPE: PRT
<213> ORGANISM: Homo sapiens

<400> SEQUENCE: 2

Met Ala Thr Ala Glu Arg Arg Ala Leu Gly Ile Gly Phe Gln Trp Leu
  1               5                  10                  15

Ser Leu Ala Thr Leu Val Leu Ile Cys Ala Gly Gln Gly Gly Arg Arg
                 20                  25                  30

Glu Asp Gly Gly Pro Ala Cys Tyr Gly Gly Phe Asp Leu Tyr Phe Ile
             35                  40                  45

Leu Asp Lys Ser Gly Ser Val Leu His His Trp Asn Glu Ile Tyr Tyr
         50                  55                  60

Phe Val Glu Gln Leu Ala His Lys Phe Ile Ser Pro Gln Leu Arg Met
 65                  70                  75                  80

Ser Phe Ile Val Phe Ser Thr Arg Gly Thr Thr Leu Met Lys Leu Thr
                 85                  90                  95

Glu Asp Arg Glu Gln Ile Arg Gln Gly Leu Glu Glu Leu Gln Lys Val
            100                 105                 110

Leu Pro Gly Gly Asp Thr Tyr Met His Glu Gly Phe Glu Arg Ala Ser
        115                 120                 125

Glu Gln Ile Tyr Tyr Glu Asn Arg Gln Gly Tyr Arg Thr Ala Ser Val
    130                 135                 140

Ile Ile Ala Leu Thr Asp Gly Glu Leu His Glu Asp Leu Phe Phe Tyr
145                 150                 155                 160

Ser Glu Arg Glu Ala Asn Arg Ser Arg Asp Leu Gly Ala Ile Val Tyr
                165                 170                 175

Cys Val Gly Val Lys Asp Phe Asn Glu Thr Gln Leu Ala Arg Ile Ala
            180                 185                 190

Asp Ser Lys Asp His Val Phe Pro Val Asn Asp Gly Phe Gln Ala Leu
        195                 200                 205

Gln Gly Ile Ile His Ser Ile Leu Lys Lys Ser Cys Ile Glu Ile Leu
    210                 215                 220

Ala Ala Glu Pro Ser Thr Ile Cys Ala Gly Glu Ser Phe Gln Val Val
225                 230                 235                 240

Val Arg Gly Asn Gly Phe Arg His Ala Arg Asn Val Asp Arg Val Leu
                245                 250                 255

Cys Ser Phe Lys Ile Asn Asp Ser Val Thr Leu Asn Glu Lys Pro Phe
            260                 265                 270

Ser Val Glu Asp Thr Tyr Leu Leu Cys Pro Ala Pro Ile Leu Lys Glu
        275                 280                 285

Val Gly Met Lys Ala Ala Leu Gln Val Ser Met Asn Asp Gly Leu Ser
    290                 295                 300
```

```
Phe Ile Ser Ser Ser Val Ile Ile Thr Thr Thr His Cys Ser Asp Gly
305                 310                 315                 320

Ser Ile Leu Ala Ile Ala Leu Leu Ile Leu Phe Leu Leu Leu Ala Leu
            325                 330                 335

Ala Leu Leu Trp Trp Phe Trp Pro Leu Cys Cys Thr Val Ile Ile Lys
            340                 345                 350

Glu Val Pro Pro Pro Ala Glu Glu Ser Glu Asn Lys Ile Lys
            355                 360             365
```

<210> SEQ ID NO 3
<211> LENGTH: 180
<212> TYPE: PRT
<213> ORGANISM: Artificial Sequence
<220> FEATURE:
<223> OTHER INFORMATION: Description of Artificial Sequence:von
      Willebrand factor A domain consensus sequence

<400> SEQUENCE: 3

```
Pro Leu Asp Val Val Phe Leu Leu Asp Gly Ser Gly Ser Met Gly Gly
1               5                   10                  15

Asn Arg Phe Glu Leu Ala Lys Glu Phe Val Lys Leu Val Glu Gln
            20                  25                  30

Leu Asp Ile Gly Pro Arg Gly Asp Arg Val Gly Leu Val Thr Phe Ser
            35                  40                  45

Ser Asp Ala Arg Val Leu Phe Pro Leu Asn Asp Ser Gln Ser Lys Asp
    50                  55                  60

Ala Leu Leu Glu Ala Leu Ala Asn Leu Ser Tyr Ser Leu Gly Gly Gly
65                  70                  75                  80

Thr Asn Leu Gly Ala Ala Leu Glu Tyr Ala Leu Glu Asn Leu Phe Ser
                85                  90                  95

Glu Ser Ala Gly Ser Arg Arg Gly Ala Pro Lys Val Leu Ile Leu Ile
            100                 105                 110

Thr Asp Gly Glu Ser Asn Asp Gly Gly Glu Asp Ile Leu Lys Ala Ala
            115                 120                 125

Lys Glu Leu Lys Arg Ser Gly Val Lys Val Phe Val Val Gly Val Gly
130                 135                 140

Asn Ala Val Asp Glu Glu Leu Lys Lys Leu Ala Ser Ala Pro Gly
145                 150                 155                 160

Gly Val Phe Ala Val Glu Asp Leu Pro Glu Leu Leu Asp Leu Leu Ile
                165                 170                 175

Asp Leu Leu Leu
            180
```

<210> SEQ ID NO 4
<211> LENGTH: 198
<212> TYPE: PRT
<213> ORGANISM: Homo sapiens

<400> SEQUENCE: 4

```
Cys Pro Ser Leu Ile Asp Val Val Val Cys Asp Glu Ser Asn Ser
1               5                   10                  15

Ile Tyr Pro Trp Asp Ala Val Lys Asn Phe Leu Glu Lys Phe Val Gln
            20                  25                  30

Gly Leu Asp Ile Gly Pro Thr Lys Thr Gln Val Gly Leu Ile Gln Tyr
            35                  40                  45

Ala Asn Asn Pro Arg Val Val Phe Asn Leu Asn Thr Tyr Lys Thr Lys
    50                  55                  60
```

-continued

```
Glu Glu Met Ile Val Ala Thr Ser Gln Thr Ser Gln Tyr Gly Gly Asp
 65                  70                  75                  80

Leu Thr Asn Thr Phe Gly Ala Ile Gln Tyr Ala Arg Lys Tyr Ala Tyr
                 85                  90                  95

Ser Ala Ser Gly Gly Arg Arg Ser Ala Ala Thr Lys Val Met Val Val
            100                 105                 110

Val Thr Asp Gly Glu Ser His Asp Gly Ser Met Leu Lys Ala Val Ile
        115                 120                 125

Asp Gln Cys Asn His Asp Asn Ile Leu Arg Phe Gly Ile Ala Val Leu
    130                 135                 140

Gly Tyr Leu Asn Arg Asn Ala Leu Asp Thr Lys Asn Leu Ile Lys Glu
145                 150                 155                 160

Ile Lys Ala Ile Ala Ser Ile Pro Thr Glu Arg Tyr Phe Phe Asn Val
                165                 170                 175

Ser Asp Glu Ala Ala Leu Leu Glu Lys Ala Gly Thr Leu Gly Glu Gln
            180                 185                 190

Ile Phe Ser Ile Glu Gly
            195
```

<210> SEQ ID NO 5
<211> LENGTH: 5540
<212> TYPE: DNA
<213> ORGANISM: Homo sapiens
<220> FEATURE:
<221> NAME/KEY: CDS
<222> LOCATION: (144)..(1835)

<400> SEQUENCE: 5

```
aattgcttcc ggggagttgc gagggagcga gggggaataa aggacccgcg aggaagggcc     60
cgcggatggc gcgtccctga gggtcgtggc gagttcgcgg agcgtgggaa ggagcggacc    120
ctgctctccc cgggctgcgg gcc atg gcc acg gcg gag cgg aga gcc ctc ggc    173
                         Met Ala Thr Ala Glu Arg Arg Ala Leu Gly
                           1               5                  10 atc ggc ttc cag tgg ctc tct ttg gcc act ctg gtg ctc atc tgc gcc     221
Ile Gly Phe Gln Trp Leu Ser Leu Ala Thr Leu Val Leu Ile Cys Ala
             15                  20                  25 ggg caa ggg gga cgc agg gag gat ggg ggt cca gcc tgc tac ggc gga     269
Gly Gln Gly Gly Arg Arg Glu Asp Gly Gly Pro Ala Cys Tyr Gly Gly
         30                  35                  40 ttt gac ctg tac ttc att ttg gac aaa tca gga agt gtg ctg cac cac     317
Phe Asp Leu Tyr Phe Ile Leu Asp Lys Ser Gly Ser Val Leu His His
     45                  50                  55 tgg aat gaa atc tat tac ttt gtg gaa cag ttg gct cac aaa ttc atc     365
Trp Asn Glu Ile Tyr Tyr Phe Val Glu Gln Leu Ala His Lys Phe Ile
 60                  65                  70 agc cca cag ttg aga atg tcc ttt att gtt ttc tcc acc cga gga aca     413
Ser Pro Gln Leu Arg Met Ser Phe Ile Val Phe Ser Thr Arg Gly Thr
 75                  80                  85                  90 acc tta atg aaa ctg aca gaa gac aga gaa caa atc cgt caa ggc cta     461
Thr Leu Met Lys Leu Thr Glu Asp Arg Glu Gln Ile Arg Gln Gly Leu
                 95                 100                 105 gaa gaa ctc cag aaa gtt ctg cca gga gga gac act tac atg cat gaa     509
Glu Glu Leu Gln Lys Val Leu Pro Gly Gly Asp Thr Tyr Met His Glu
            110                 115                 120 gga ttt gaa agg gcc agt gag cag att tat tat gaa aac aga caa ggg     557
Gly Phe Glu Arg Ala Ser Glu Gln Ile Tyr Tyr Glu Asn Arg Gln Gly
        125                 130                 135
```

| | | |
|---|---|---|
| tac agg aca gcc agc gtc atc att gct ttg act gat gga gaa ctc cat<br>Tyr Arg Thr Ala Ser Val Ile Ile Ala Leu Thr Asp Gly Glu Leu His<br>140                          145                         150 | | 605 |
| gaa gat ctc ttt ttc tat tca gag agg gag gct aat agg tct cga gat<br>Glu Asp Leu Phe Phe Tyr Ser Glu Arg Glu Ala Asn Arg Ser Arg Asp<br>155                          160                        165                        170 | | 653 |
| ctt ggt gca att gtt tac tgt gtt ggt gtg aaa gat ttc aat gag aca<br>Leu Gly Ala Ile Val Tyr Cys Val Gly Val Lys Asp Phe Asn Glu Thr<br>                                  175                        180                        185 | | 701 |
| cag ctg gcc cgg att gcg gac agt aag gat cat gtg ttt ccc gtg aat<br>Gln Leu Ala Arg Ile Ala Asp Ser Lys Asp His Val Phe Pro Val Asn<br>                 190                        195                        200 | | 749 |
| gac ggc ttt cag gct ctg caa ggc atc atc cac tca att ttg aag aag<br>Asp Gly Phe Gln Ala Leu Gln Gly Ile Ile His Ser Ile Leu Lys Lys<br>                 205                        210                        215 | | 797 |
| tcc tgc atc gaa att cta gca gct gaa cca tcc acc ata tgt gca gga<br>Ser Cys Ile Glu Ile Leu Ala Ala Glu Pro Ser Thr Ile Cys Ala Gly<br>220                          225                         230 | | 845 |
| gag tca ttt caa gtt gtc gtg aga gga aac ggc ttc cga cat gcc cgc<br>Glu Ser Phe Gln Val Val Val Arg Gly Asn Gly Phe Arg His Ala Arg<br>235                          240                        245                        250 | | 893 |
| aac gtg gac agg gtc ctc tgc agc ttc aag atc aat gac tcg gtc aca<br>Asn Val Asp Arg Val Leu Cys Ser Phe Lys Ile Asn Asp Ser Val Thr<br>                                  255                        260                        265 | | 941 |
| ctc aat gag aag ccc ttt tct gtg gaa gat act tat tta ctg tgt cca<br>Leu Asn Glu Lys Pro Phe Ser Val Glu Asp Thr Tyr Leu Leu Cys Pro<br>                 270                        275                        280 | | 989 |
| gcg cct atc tta aaa gaa gtt ggc atg aaa gct gca ctc cag gtc agc<br>Ala Pro Ile Leu Lys Glu Val Gly Met Lys Ala Ala Leu Gln Val Ser<br>                 285                        290                        295 | | 1037 |
| atg aac gat ggc ctc tct ttt atc tcc agt tct gtc atc atc acc acc<br>Met Asn Asp Gly Leu Ser Phe Ile Ser Ser Ser Val Ile Ile Thr Thr<br>300                          305                         310 | | 1085 |
| aca cac tgt tct gac ggt tcc atc ctg gcc atc gcc ctg ctg atc ctg<br>Thr His Cys Ser Asp Gly Ser Ile Leu Ala Ile Ala Leu Leu Ile Leu<br>315                          320                        325                        330 | | 1133 |
| ttc ctg ctc cta gcc ctg gct ctc ctc tgg tgg ttc tgg ccc ctc tgc<br>Phe Leu Leu Leu Ala Leu Ala Leu Leu Trp Trp Phe Trp Pro Leu Cys<br>                 335                        340                        345 | | 1181 |
| tgc act gtg att atc aag gag gtc cct cca ccc cct gcc gag gag agt<br>Cys Thr Val Ile Ile Lys Glu Val Pro Pro Pro Pro Ala Glu Glu Ser<br>                     350                        355                        360 | | 1229 |
| gag gaa gaa gat gat gat ggt ctg cct aag aaa aag tgg cca acg gta<br>Glu Glu Glu Asp Asp Asp Gly Leu Pro Lys Lys Lys Trp Pro Thr Val<br>                 365                        370                        375 | | 1277 |
| gac gcc tct tat tat ggt ggg aga ggc gtt gga ggc att aaa aga atg<br>Asp Ala Ser Tyr Tyr Gly Gly Arg Gly Val Gly Gly Ile Lys Arg Met<br>380                          385                         390 | | 1325 |
| gag gtt cgt tgg gga gaa aag ggc tcc aca gaa gaa ggt gct aag ttg<br>Glu Val Arg Trp Gly Glu Lys Gly Ser Thr Glu Glu Gly Ala Lys Leu<br>395                          400                        405                        410 | | 1373 |
| gaa aag gca aag aat gca aga gtc aag atg ccg gag cag gaa tat gaa<br>Glu Lys Ala Lys Asn Ala Arg Val Lys Met Pro Glu Gln Glu Tyr Glu<br>                 415                        420                        425 | | 1421 |
| ttc cct gag ccg cga aat ctc aac aac aat atg cgt cgg cct tct tcc<br>Phe Pro Glu Pro Arg Asn Leu Asn Asn Asn Met Arg Arg Pro Ser Ser<br>                     430                        435                        440 | | 1469 |
| ccc cgg aag tgg tac tct cca atc aag gga aaa ctc gat gcc ttg tgg<br>Pro Arg Lys Trp Tyr Ser Pro Ile Lys Gly Lys Leu Asp Ala Leu Trp<br>                 445                        450                        455 | | 1517 |

| | | |
|---|---|---|
| gtc cta ctg agg aaa gga tat gat cgt gtg tct gtg atg cgt cca cag<br>Val Leu Leu Arg Lys Gly Tyr Asp Arg Val Ser Val Met Arg Pro Gln<br>460                                465                      470 | 1565 | |
| cca gga gac acg ggg cgc tgc atc aac ttc acc agg gtc aag aac aac<br>Pro Gly Asp Thr Gly Arg Cys Ile Asn Phe Thr Arg Val Lys Asn Asn<br>475                          480                      485                      490 | 1613 | |
| cag cca gcc aag tac cca ctc aac aac gcc tac cac acc tcc tcg ccg<br>Gln Pro Ala Lys Tyr Pro Leu Asn Asn Ala Tyr His Thr Ser Ser Pro<br>                      495                      500                      505 | 1661 | |
| cct cct gcc ccc atc tac act ccc cca cct cct gcg ccc cac tgc cct<br>Pro Pro Ala Pro Ile Tyr Thr Pro Pro Pro Ala Pro His Cys Pro<br>                510                      515                      520 | 1709 | |
| ccc ccg ccc ccc agc gcc cct acc cct ccc atc ccg tcc cca cct tcc<br>Pro Pro Pro Pro Ser Ala Pro Thr Pro Pro Ile Pro Ser Pro Pro Ser<br>                525                      530                      535 | 1757 | |
| acc ctt ccc cct cct ccc cag gct cca cct ccc aac agg gca cct cct<br>Thr Leu Pro Pro Pro Pro Gln Ala Pro Pro Pro Asn Arg Ala Pro Pro<br>      540                      545                      550 | 1805 | |
| ccc tcc cgc cct cct cca agg cct tct gtc tagagcccaa agttcctgct<br>Pro Ser Arg Pro Pro Pro Arg Pro Ser Val<br>555                    560 | 1855 | |
| ctgggctctc tcagaaactt caggagatgt tagaacaagt cttccagtt agagaagagg | 1915 | |
| agtggtgata aagcccactg accttcacac attctaaaaa ttggttggca atgccagtat | 1975 | |
| accaacaatc atgatcagct gaaagaaaca gatattttaa attgccagaa aacaaatgat | 2035 | |
| gaggcaacta cagtcagatt tatagccagc catctatcac ctctagaagg ttccagagac | 2095 | |
| agtgaaactg caagatgctc tcaacaggat tatgtctcat ggagaccagt aagaaaatca | 2155 | |
| tttatctgaa ggtgaaatgc agagttggat aagaaataca ttgctgggtt tctaaaatgc | 2215 | |
| tgccttcctg cctctactcc acctccatcc ctggactttg dcccttggc ctaggagcct | 2275 | |
| aaggaccttc acccctgtgc accacccaag aaagaggaaa actttgccta caactttgga | 2335 | |
| aatgctgggg tccctggtgt ggtaagaaac tcaacatcag acgggtatgc agaaggatgt | 2395 | |
| tcttctggga tttgcaggta cataaaaaat gtatggcatc ttttccttgc aaattcttcc | 2455 | |
| agtttccaag tgagaagggg agcaggtgtt tactgatgga aaaggtatgt tgctatgttg | 2515 | |
| atgtgtaagt gaaatcagtt gtgtgcaata gacaggggcg tattcatggg agcatcagcc | 2575 | |
| agtttctaaa acccacaggc catcagcagc tagaggtggc tggctttggc cagacatgga | 2635 | |
| ccctaaatca acagacaatg gcattgtcga gagcaaccct gttaatgaat catgttaaaa | 2695 | |
| atcaaggttt ggcttcagtt taaatcactt gaggtatgaa gtttatcctg ttttccagag | 2755 | |
| ataaacataa gttgatcttc ccaaaatacc atcattagga cctatcacac aatatcacta | 2815 | |
| gttttttttg tttgtttgtt ttttgttttt tttcttggta aagccatgca ccacagactt | 2875 | |
| ctgggcagag ctgagagaca atggtcctga cataataagg atctttgatt aaccccata | 2935 | |
| aggcatgtgt gtgtatacaa atatacttct ctttggcttt tcgacataga acctcagctg | 2995 | |
| ttaaccaagg ggaaatacat cagatctgca acacagaaat gctctgcctg aaatttccac | 3055 | |
| catgcctagg actcaccca tttatccagg tctttctgga tctgtttaat caataagccc | 3115 | |
| tataatcact tgctaaacac tgggcttcat caccaggga taaaacaga gatcattgtc | 3175 | |
| ttggacctcc tgcatcagcc tattcaaaat tatctctctc tctagctttc acaaatcct | 3235 | |
| aaaattcctg tcccaagcca cccaattct cagatctttt ctggaacaag gcagaatata | 3295 | |
| aaataaatat acatttagtg gcttgggcta tggtctccaa agatccttca aaatacatc | 3355 | |

```
aagccagctt cattcactca ctttacttag aacagagata taagggcctg ggatgcattt      3415
attttatcaa taccaatttt tgtggccatg gcagacattg ctaatcaatc acagcactat      3475
ttcctattaa gcccactgat ttcttcacaa tccttctcaa attacaattc caaagagccg      3535
ccactcaaca gtcagatgaa cccaacagtc agatgagaga aatgaaccct acttgctatc      3595
tctatcttag aaagcaaaaa caaacaggag tttccaggga gaatgggaaa gccaggggc      3655
ataaaaggta cagtcagggg aaaatagatc taggcagagt gccttagtca gggaccacgg      3715
gcgctgaatc tgcagtgcca acaccaaact gacacatctc caggtgtacc tccaaccta      3775
gccttctccc acagctgcct acaacagagt ctcccagcct tctcagagag ctaaaaccag      3835
aaatttccag actcatgaaa gcaaccccc agcctctccc caaccctgcc gcattgtcta      3895
attttagaa cactaggctt cttctttcat gtagttcctc ataagcaggg gccagaatat      3955
ctcagccacc tgcagtgaca ttgctggacc cctgaaaacc attccatagg agaatgggtt      4015
ccccaggctc acagtgtaga gacattgagc ccatcacaac tgttttgact gctggcagtc      4075
taaaacagtc cacccacccc atggcactgc cgcgtgattc ccgcggccat tcagaagttc      4135
aagccgagat gctgacgttg ctgagcaacg agatggtgag catcagtgca aatgcaccat      4195
tcagcacatc agtcatatgc ccagtgcagt tacaagatgt tgtttcggca aagcattttg      4255
atggaatagg gaactgcaaa tgtatgatga ttttgaaaag gctcagcagg atttgttctt      4315
aaaccgactc agtgtgtcat ccccggttat ttagaattac agttaagaag gagaaacttc      4375
tataagactg tatgaacaag gtgatatctt catagtgggc tattacaggc aggaaaatgt      4435
tttaactggt ttacaaaatc catcaatact tgtgtcattc cctgtaaaag gcaggagaca      4495
tgtgattatg atcaggaaac tgcacaaaat tattgttttc agccccgtg ttattgtcct       4555
tttgaactgt ttttttttta ttaaagccaa atttgtgttg tatatattcg tattccatgt      4615
gttagatgga agcatttcct atccagtgtg aataaaaaga acagttgtag taaattatta      4675
taaagccgat gatatttcat ggcaggttat tctaccaagc tgtgcttgtt ggtttttccc      4735
atgactgtat tgcttttata aatgtacaaa tagttactga aatgacgaga cccttgtttg      4795
cacagcatta ataagaacct tgataagaac catattctgt tgacagccag ctcacagttt      4855
cttgcctgaa gcttggtgca ccctccagtg agacacaaga tctctctttt accaaagttg      4915
agaacagagc tggtggatta ttaatagtc ttcgatatct ggccatgggt aacctcattg       4975
taactatcat cagaatgggc agagatgatc ttgaagtgtc acatacacta aagtccaaac      5035
actatgtcag atggggtaa aatccattaa agaacaggaa aaaataatta taagatgata       5095
agcaaatgtt tcagcccaat gtcaacccag ttaaaaaaaa aattaatgct gtgtaaaatg      5155
gttgaattag tttgcaaact atataaagac atatgcagta aaaagtctgt taatgcacat      5215
cctgtgggaa tggagtgttc taaccaattg ccttttcttg ttatctgagc tctcctatat      5275
tatcatactc agataaccaa attaaagaa ttagaatatg attttaata cacttaacat        5335
taaactcttc taactttctt ctttctgtga taattcagaa gatagttatg gatcttcaat      5395
gcctctgagt cattgttata aaaatcagt tatcactata ccatgctata ggagactggg       5455
caaaacctgt acaatgacaa ccctggaagt tgcttttttt aaaaaaataa taaatttctt      5515
aaatcaaaaa aaaaaaaaaa aaaaa                                            5540
```

<210> SEQ ID NO 6
<211> LENGTH: 564
<212> TYPE: PRT
<213> ORGANISM: Homo sapiens

<400> SEQUENCE: 6

```
Met Ala Thr Ala Glu Arg Arg Ala Leu Gly Ile Gly Phe Gln Trp Leu
 1               5                  10                  15

Ser Leu Ala Thr Leu Val Leu Ile Cys Ala Gly Gln Gly Gly Arg Arg
             20                  25                  30

Glu Asp Gly Gly Pro Ala Cys Tyr Gly Gly Phe Asp Leu Tyr Phe Ile
         35                  40                  45

Leu Asp Lys Ser Gly Ser Val Leu His His Trp Asn Glu Ile Tyr Tyr
     50                  55                  60

Phe Val Glu Gln Leu Ala His Lys Phe Ile Ser Pro Gln Leu Arg Met
 65                  70                  75                  80

Ser Phe Ile Val Phe Ser Thr Arg Gly Thr Thr Leu Met Lys Leu Thr
                 85                  90                  95

Glu Asp Arg Glu Gln Ile Arg Gln Gly Leu Glu Glu Leu Gln Lys Val
            100                 105                 110

Leu Pro Gly Gly Asp Thr Tyr Met His Glu Gly Phe Glu Arg Ala Ser
        115                 120                 125

Glu Gln Ile Tyr Tyr Glu Asn Arg Gln Gly Tyr Arg Thr Ala Ser Val
    130                 135                 140

Ile Ile Ala Leu Thr Asp Gly Glu Leu His Glu Asp Leu Phe Phe Tyr
145                 150                 155                 160

Ser Glu Arg Glu Ala Asn Arg Ser Arg Asp Leu Gly Ala Ile Val Tyr
                165                 170                 175

Cys Val Gly Val Lys Asp Phe Asn Glu Thr Gln Leu Ala Arg Ile Ala
            180                 185                 190

Asp Ser Lys Asp His Val Phe Pro Val Asn Asp Gly Phe Gln Ala Leu
        195                 200                 205

Gln Gly Ile Ile His Ser Ile Leu Lys Lys Ser Cys Ile Glu Ile Leu
    210                 215                 220

Ala Ala Glu Pro Ser Thr Ile Cys Ala Gly Glu Ser Phe Gln Val Val
225                 230                 235                 240

Val Arg Gly Asn Gly Phe Arg His Ala Arg Asn Val Asp Arg Val Leu
                245                 250                 255

Cys Ser Phe Lys Ile Asn Asp Ser Val Thr Leu Asn Glu Lys Pro Phe
            260                 265                 270

Ser Val Glu Asp Thr Tyr Leu Leu Cys Pro Ala Pro Ile Leu Lys Glu
        275                 280                 285

Val Gly Met Lys Ala Ala Leu Gln Val Ser Met Asn Asp Gly Leu Ser
    290                 295                 300

Phe Ile Ser Ser Ser Val Ile Ile Thr Thr Thr His Cys Ser Asp Gly
305                 310                 315                 320

Ser Ile Leu Ala Ile Ala Leu Leu Ile Leu Phe Leu Leu Leu Ala Leu
                325                 330                 335

Ala Leu Leu Trp Trp Phe Trp Pro Leu Cys Cys Thr Val Ile Ile Lys
            340                 345                 350

Glu Val Pro Pro Pro Ala Glu Glu Ser Glu Glu Asp Asp Asp
        355                 360                 365

Gly Leu Pro Lys Lys Trp Pro Thr Val Asp Ala Ser Tyr Tyr Gly
    370                 375                 380

Gly Arg Gly Val Gly Gly Ile Lys Arg Met Glu Val Arg Trp Gly Glu
385                 390                 395                 400
```

-continued

```
Lys Gly Ser Thr Glu Glu Gly Ala Lys Leu Glu Lys Ala Lys Asn Ala
            405                 410                 415

Arg Val Lys Met Pro Glu Gln Glu Tyr Glu Phe Pro Glu Pro Arg Asn
            420                 425                 430

Leu Asn Asn Asn Met Arg Arg Pro Ser Ser Pro Arg Lys Trp Tyr Ser
            435                 440                 445

Pro Ile Lys Gly Lys Leu Asp Ala Leu Trp Val Leu Leu Arg Lys Gly
    450                 455                 460

Tyr Asp Arg Val Ser Val Met Arg Pro Gln Pro Gly Asp Thr Gly Arg
465                 470                 475                 480

Cys Ile Asn Phe Thr Arg Val Lys Asn Asn Gln Pro Ala Lys Tyr Pro
                485                 490                 495

Leu Asn Asn Ala Tyr His Thr Ser Pro Pro Ala Pro Ile Tyr
                500                 505                 510

Thr Pro Pro Pro Ala Pro His Cys Pro Pro Pro Pro Ser Ala
                515                 520                 525

Pro Thr Pro Pro Ile Pro Ser Pro Ser Thr Leu Pro Pro Pro
            530                 535                 540

Gln Ala Pro Pro Pro Asn Arg Ala Pro Pro Ser Arg Pro Pro Pro
545                 550                 555                 560

Arg Pro Ser Val
```

<210> SEQ ID NO 7
<211> LENGTH: 2112
<212> TYPE: DNA
<213> ORGANISM: Homo sapiens
<220> FEATURE:
<221> NAME/KEY: CDS
<222> LOCATION: (113)..(1111)

<400> SEQUENCE: 7

```
ggggaataaa ggacccgcga ggaagggccc gcggatggcg cgtccctgag ggtcgtggcg      60
agttcgcgga gcgtgggaag gagcggaccc tgctctcccc gggctgcggg cc atg gcc    118
                                                           Met Ala
                                                             1 acg gcg gag cgg aga gcc ctc ggc atc ggc ttc cag tgg ctc tct ttg      166
Thr Ala Glu Arg Arg Ala Leu Gly Ile Gly Phe Gln Trp Leu Ser Leu
         5                  10                  15 gcc act ctg gtg ctc atc tgc gcc ggg caa ggg gga cgc agg gag gat      214
Ala Thr Leu Val Leu Ile Cys Ala Gly Gln Gly Gly Arg Arg Glu Asp
     20                  25                  30 ggg ggt cca gcc tgc tac ggc gga ttt gac ctg tac ttc att ttg gac      262
Gly Gly Pro Ala Cys Tyr Gly Gly Phe Asp Leu Tyr Phe Ile Leu Asp
 35                  40                  45                  50 aaa tca gga agt gtg ctg cac cac tgg aat gaa atc tat tac ttt gtg      310
Lys Ser Gly Ser Val Leu His His Trp Asn Glu Ile Tyr Tyr Phe Val
                 55                  60                  65 gaa cag ttg gct cac aaa ttc atc agc cca cag ttg aga atg tcc ttt      358
Glu Gln Leu Ala His Lys Phe Ile Ser Pro Gln Leu Arg Met Ser Phe
             70                  75                  80 att gtt ttc tcc acc cga gga aca acc tta atg aaa ctg aca gaa gac      406
Ile Val Phe Ser Thr Arg Gly Thr Thr Leu Met Lys Leu Thr Glu Asp
         85                  90                  95 aga gaa caa atc cgt caa ggc cta gaa gaa ctc cag aaa gtt ctg cca      454
Arg Glu Gln Ile Arg Gln Gly Leu Glu Glu Leu Gln Lys Val Leu Pro
    100                 105                 110
```

```
gga gga gac act tac atg cat gaa gga ttt gaa agg gcc agt gag cag        502
Gly Gly Asp Thr Tyr Met His Glu Gly Phe Glu Arg Ala Ser Glu Gln
115                 120                 125                 130 att tat tat gaa aac aga caa ggg tac agg aca gcc agc gtc atc att        550
Ile Tyr Tyr Glu Asn Arg Gln Gly Tyr Arg Thr Ala Ser Val Ile Ile
                135                 140                 145 gct ttg act gat gga gaa ctc cat gaa gat ctc ttt ttc tat tca gag        598
Ala Leu Thr Asp Gly Glu Leu His Glu Asp Leu Phe Phe Tyr Ser Glu
        150                 155                 160 agg gag gct aat agg tct cga gat ctt ggt gca att gtt tac tgt gtt        646
Arg Glu Ala Asn Arg Ser Arg Asp Leu Gly Ala Ile Val Tyr Cys Val
165                 170                 175 ggt gtg aaa gat ttc aat gag aca cag ctg gcc cgg att gcg gac agt        694
Gly Val Lys Asp Phe Asn Glu Thr Gln Leu Ala Arg Ile Ala Asp Ser
    180                 185                 190 aag gat cat gtg ttt ccc gtg aat gac ggc ttt cag gct ctg caa ggc        742
Lys Asp His Val Phe Pro Val Asn Asp Gly Phe Gln Ala Leu Gln Gly
195                 200                 205                 210 atc atc cac tca att ttg aag aag tcc tgc atc gaa att cta gca gct        790
Ile Ile His Ser Ile Leu Lys Lys Ser Cys Ile Glu Ile Leu Ala Ala
                215                 220                 225 gaa cca tcc acc ata tgt gca gga gag tca ttt caa gtt gtc gtg aga        838
Glu Pro Ser Thr Ile Cys Ala Gly Glu Ser Phe Gln Val Val Val Arg
        230                 235                 240 gga aac ggc ttc cga cat gcc cgc aac gtg gac agg gtc ctc tgc agc        886
Gly Asn Gly Phe Arg His Ala Arg Asn Val Asp Arg Val Leu Cys Ser
            245                 250                 255 ttc aag atc aat gac tcg gtc aca ctc aat gag aag ccc ttt tct gtg        934
Phe Lys Ile Asn Asp Ser Val Thr Leu Asn Glu Lys Pro Phe Ser Val
260                 265                 270 gaa gat act tat tta ctg tgt cca gcg cct atc tta aaa gaa gtt ggc        982
Glu Asp Thr Tyr Leu Leu Cys Pro Ala Pro Ile Leu Lys Glu Val Gly
275                 280                 285                 290 atg aaa gct gca ctc cag gtc agc atg aac gat ggc ctc tct ttt atc       1030
Met Lys Ala Ala Leu Gln Val Ser Met Asn Asp Gly Leu Ser Phe Ile
                295                 300                 305 tcc agt tct gtc atc atc acc acc aca cac tgt agc ctc cac aaa att       1078
Ser Ser Ser Val Ile Ile Thr Thr Thr His Cys Ser Leu His Lys Ile
        310                 315                 320 gca tca ggc ccc aca aca gct gct tgc atg gaa tagcagagaa taccgcctgc     1131
Ala Ser Gly Pro Thr Thr Ala Ala Cys Met Glu
            325                 330 tccctccgga cagcacactc ctgaaaacgg ggagagagga gccaaacatg ctcggtttac     1191
actttcctta tttactgaat gagtggaggg cagagacagg cctggagtta cgcacactga     1251
gtgccccaac atggaaagaa acatcaggag ggacaggaaa cgttccctcc ttaaccaaca     1311
gttttcaaga ccttactgga ggcactttat tggctacata atcactccat gcggtgggca     1371
tcaggcagaa tcctggtgca gacccaactt tgaggtggag gatttcacag tttctttatt     1431
ttgaacttcc cccaggctcc cactaattcc tctccattct atcctcctcc ctttcccaca     1491
aaagaaaaca gaaaggagca gcagtgtttg ataccgtatc atccagaggc ctggttctct     1551
cccattatag ggcaaacaag ccctggcaag atatttcact cccgcccat gccatgcatt      1611 aaaaatccaa aattgcctat attccacctg ccaagcaaga gatgctttca ttattgaagt     1671
tccaaatgta tacctttgag aacagtgcct tctcgtctta aaagagaggt cctcattttg     1731
tgagttggga gcagagggaa ttaaagaaag ccatgatgca gggatttggc cattcaagcc     1791
```

-continued

```
gggcagcctt cagagaatgt catccctaat gacacatgcc cgaatgaagg agcggggctg   1851
agcttgtcct gccttcgtat tgaatgttgc ctgtctgcct ccttaatagc gggcctctgt   1911
gtgagcattt gacaagactt aaaactattc attgaagaaa atggatgatc ccccaacagg   1971
aagatgcaac cccatgggct gcctgcttga ccacagaagt gcttccagct ccagttgctc   2031
atctgagaac tccccccacc acttgctgtt aaaattgtta aaattaaagg ccatgttgat   2091
tgaaaaaaaa aaaaaaaaaa a                                             2112
```

<210> SEQ ID NO 8
<211> LENGTH: 333
<212> TYPE: PRT
<213> ORGANISM: Homo sapiens

<400> SEQUENCE: 8

```
Met Ala Thr Ala Glu Arg Arg Ala Leu Gly Ile Gly Phe Gln Trp Leu
 1               5                  10                  15

Ser Leu Ala Thr Leu Val Leu Ile Cys Ala Gly Gln Gly Gly Arg Arg
            20                  25                  30

Glu Asp Gly Gly Pro Ala Cys Tyr Gly Gly Phe Asp Leu Tyr Phe Ile
        35                  40                  45

Leu Asp Lys Ser Gly Ser Val Leu His His Trp Asn Glu Ile Tyr Tyr
    50                  55                  60

Phe Val Glu Gln Leu Ala His Lys Phe Ile Ser Pro Gln Leu Arg Met
65                  70                  75                  80

Ser Phe Ile Val Phe Ser Thr Arg Gly Thr Thr Leu Met Lys Leu Thr
                85                  90                  95

Glu Asp Arg Glu Gln Ile Arg Gln Gly Leu Glu Glu Leu Gln Lys Val
            100                 105                 110

Leu Pro Gly Gly Asp Thr Tyr Met His Glu Gly Phe Glu Arg Ala Ser
        115                 120                 125

Glu Gln Ile Tyr Tyr Glu Asn Arg Gln Gly Tyr Arg Thr Ala Ser Val
    130                 135                 140

Ile Ile Ala Leu Thr Asp Gly Glu Leu His Glu Asp Leu Phe Phe Tyr
145                 150                 155                 160

Ser Glu Arg Glu Ala Asn Arg Ser Arg Asp Leu Gly Ala Ile Val Tyr
                165                 170                 175

Cys Val Gly Val Lys Asp Phe Asn Glu Thr Gln Leu Ala Arg Ile Ala
            180                 185                 190

Asp Ser Lys Asp His Val Phe Pro Val Asn Asp Gly Phe Gln Ala Leu
        195                 200                 205

Gln Gly Ile Ile His Ser Ile Leu Lys Lys Ser Cys Ile Glu Ile Leu
    210                 215                 220

Ala Ala Glu Pro Ser Thr Ile Cys Ala Gly Glu Ser Phe Gln Val Val
225                 230                 235                 240

Val Arg Gly Asn Gly Phe Arg His Ala Arg Asn Val Asp Arg Val Leu
                245                 250                 255

Cys Ser Phe Lys Ile Asn Asp Ser Val Thr Leu Asn Glu Lys Pro Phe
            260                 265                 270

Ser Val Glu Asp Thr Tyr Leu Leu Cys Pro Ala Pro Ile Leu Lys Glu
        275                 280                 285

Val Gly Met Lys Ala Ala Leu Gln Val Ser Met Asn Asp Gly Leu Ser
    290                 295                 300

Phe Ile Ser Ser Ser Val Ile Ile Thr Thr Thr His Cys Ser Leu His
305                 310                 315                 320
```

-continued

```
Lys Ile Ala Ser Gly Pro Thr Thr Ala Ala Cys Met Glu
            325                 330
```

<210> SEQ ID NO 9
<211> LENGTH: 1436
<212> TYPE: DNA
<213> ORGANISM: Homo sapiens
<220> FEATURE:
<221> NAME/KEY: CDS
<222> LOCATION: (380)..(1033)

<400> SEQUENCE: 9

```
aattgcttcc ggggagttgc gagggagcga gggggaataa aggacccgcg aggaagggcc    60
cgcggatggc gcgtccctga gggtcgtggc gagttcgcgg agcgtgggaa ggagcggacc   120
ctgctctccc cgggctgcgg gccatggcca cggcggagcg gagagccctc ggcatcggct   180
tccagtggct ctcacggcca ctctggtgct catctgcgcc gggcaagggg gacgcaggga   240 ggatggggt ccagcctgct acggcggatt tgacctgtac ttcatttgg acaaatcagg    300 aagtgtgctg caccactgga atgaaatcta ttactttgtg aacagttgg ctcacaaatt    360 catcagccca cagttgaga atg tcc ttt att gtt ttc tcc acc cga gga aca   412
                      Met Ser Phe Ile Val Phe Ser Thr Arg Gly Thr
                        1               5                  10 acc tta atg aaa ctg aca gaa gac aga gaa caa atc cgt caa ggc cta    460
Thr Leu Met Lys Leu Thr Glu Asp Arg Glu Gln Ile Arg Gln Gly Leu
            15                  20                  25 gaa gaa ctc cag aaa gtt ctg cca gga gga gac act tac atg cat gaa    508
Glu Glu Leu Gln Lys Val Leu Pro Gly Gly Asp Thr Tyr Met His Glu
        30                  35                  40 gga ttt gaa agg gcc agt gag cag att tat tat gaa aac aga caa ggg    556
Gly Phe Glu Arg Ala Ser Glu Gln Ile Tyr Tyr Glu Asn Arg Gln Gly
    45                  50                  55 tac agg aca gct agc gtc atc att gct ttg act gat gga gaa ctc cat    604
Tyr Arg Thr Ala Ser Val Ile Ile Ala Leu Thr Asp Gly Glu Leu His
60                  65                  70                  75 gaa gat ctc ttt ttc tat tca gag agg gag gct aat agg tct cga gat    652
Glu Asp Leu Phe Phe Tyr Ser Glu Arg Glu Ala Asn Arg Ser Arg Asp
                80                  85                  90 ctt ggt gca att gtt tac tgt gtt ggt gtg aaa gat ttc aat gag aca    700
Leu Gly Ala Ile Val Tyr Cys Val Gly Val Lys Asp Phe Asn Glu Thr
            95                  100                 105 cag ctg gcc cgg att gcg gac agt aag gat cat gtg ttt ccc gtg aat    748
Gln Leu Ala Arg Ile Ala Asp Ser Lys Asp His Val Phe Pro Val Asn
        110                 115                 120 gac ggc ttt cag gct ctg caa ggc atc atc cac tca att ttg aag aag    796
Asp Gly Phe Gln Ala Leu Gln Gly Ile Ile His Ser Ile Leu Lys Lys
    125                 130                 135 tcc tgc atc gaa att cta gca gct gaa cca tcc acc ata tgt gca gga    844
Ser Cys Ile Glu Ile Leu Ala Ala Glu Pro Ser Thr Ile Cys Ala Gly
140                 145                 150                 155 gag tca ttt caa gtt gtc gtg aga gga aac ggc ttc cga cat gcc cgc    892
Glu Ser Phe Gln Val Val Val Arg Gly Asn Gly Phe Arg His Ala Arg
                160                 165                 170 aac gtg gac agg gtc ctc tgc agc ttc aag atc aat gac tcg gtc aca    940
Asn Val Asp Arg Val Leu Cys Ser Phe Lys Ile Asn Asp Ser Val Thr
            175                 180                 185
```

```
ctc agt aag tcc ttg cag agt cca tgg gtt tct tcg aca agt ggc ttc    988
Leu Ser Lys Ser Leu Gln Ser Pro Trp Val Ser Ser Thr Ser Gly Phe
        190                 195                 200 aag gaa ggg aat tcc cac cct tgt ctt cca gca agg cca cac aca        1033
Lys Glu Gly Asn Ser His Pro Cys Leu Pro Ala Arg Pro His Thr
205                 210                 215 tgaaaccagc agaaaagagt cttatttgct ggaaagaccc ccagcaaggg catagtgagc  1093
ccttacagtg gttccagtca gaaaaggcac cacttgggtg ggcacagccc catgggtgtc  1153
caacttggta agcagagcaa ggctggactt gagtccccgt cctccacaaa acacagagcc  1213
acaagcccca gccctgcagc agccctccgg aagcagcggg gcactggttt ccttgtcccc  1273
tgccatctac cgagtggctc actctcaggt gggagtgctg gtgatggtta attaggactg  1333
cagaaacatg agcctcctta acaaagtatt gggactctta agggtaagtg tgaaaaagga  1393
atggtctaaa tgcattaatc ttgaataaac cgaaaaccaa acc                    1436

<210> SEQ ID NO 10
<211> LENGTH: 218
<212> TYPE: PRT
<213> ORGANISM: Homo sapiens

<400> SEQUENCE: 10

Met Ser Phe Ile Val Phe Ser Thr Arg Gly Thr Thr Leu Met Lys Leu
  1               5                  10                  15

Thr Glu Asp Arg Glu Gln Ile Arg Gln Gly Leu Glu Glu Leu Gln Lys
             20                  25                  30

Val Leu Pro Gly Gly Asp Thr Tyr Met His Glu Gly Phe Glu Arg Ala
         35                  40                  45

Ser Glu Gln Ile Tyr Tyr Glu Asn Arg Gln Gly Tyr Arg Thr Ala Ser
     50                  55                  60

Val Ile Ala Leu Thr Asp Gly Glu Leu His Glu Asp Leu Phe Phe
 65                  70                  75                  80

Tyr Ser Glu Arg Glu Ala Asn Arg Ser Arg Asp Leu Gly Ala Ile Val
                 85                  90                  95

Tyr Cys Val Gly Val Lys Asp Phe Asn Glu Thr Gln Leu Ala Arg Ile
            100                 105                 110

Ala Asp Ser Lys Asp His Val Phe Pro Val Asn Asp Gly Phe Gln Ala
        115                 120                 125

Leu Gln Gly Ile Ile His Ser Ile Leu Lys Lys Ser Cys Ile Glu Ile
    130                 135                 140

Leu Ala Ala Glu Pro Ser Thr Ile Cys Ala Gly Glu Ser Phe Gln Val
145                 150                 155                 160

Val Val Arg Gly Asn Gly Phe Arg His Ala Arg Asn Val Asp Arg Val
                165                 170                 175

Leu Cys Ser Phe Lys Ile Asn Asp Ser Val Thr Leu Ser Lys Ser Leu
            180                 185                 190

Gln Ser Pro Trp Val Ser Ser Thr Ser Gly Phe Lys Glu Gly Asn Ser
        195                 200                 205

His Pro Cys Leu Pro Ala Arg Pro His Thr
    210                 215
```

RECEPTOR FOR B ANTHRACIS TOXIN

CROSS-REFERENCE TO RELATED APPLICATIONS

This application claims the benefit of U.S. provisional application Ser. No. 60/251,481, filed on Dec. 5, 2000, which is incorporated herein by reference as if set forth in its entirety.

STATEMENT REGARDING FEDERALLY SPONSORED RESEARCH OR DEVELOPMENT

This invention was made with United States government support awarded by the following agencies:
NIH AI48489 and NIH AI22021.
The United States has certain rights in this invention.

BACKGROUND OF THE INVENTION

*Bacillus anthracis*, the spore-forming causative agent of anthrax, generally infects herbivores (Hanna, 1998). Human infection, while rare, can result in a generally benign, self-limiting cutaneous disease or a systemic disease that rapidly leads to death in a high percentage of cases. The cutaneous disease can arise when spore particles from soil or animal products are introduced into cuts or skin abrasions. In contrast, the systemic disease can arise when *B. anthracis* spore particles are inhaled ($LD_{50} \approx 10,000$ spore particles). The high mortality rate and the ability to readily prepare and deliver *B. anthracis* spore particles as an aerosol have made *B. anthracis* a dreaded agent of biowarfare and bioterrorism.

The causative agent of the systemic disease is anthrax toxin (AT), which itself comprises a pair of binary, AB-type toxins—lethal toxin and edema toxin (Leppla, 1995). Each is assembled at the surface of mammalian cells from proteins released by *B. anthracis*. Lethal toxin, assembled from Protective Antigen (PA, 83 kDa) and Lethal Factor (LF, 90 kDa), is primarily responsible for lethality (Friedlander, 1986; Hanna et al., 1992; Hanna et al., 1993). Edema toxin, assembled from PA and Edema Factor (EF, 89 kDa), causes edema at the site of injection (Leppla, 1982). EF has calmodulin-dependent adenylate cyclase activity. LF is a $Zn^{++}$-dependent protease that cleaves certain proteins involved in signal transduction and cell cycle progression (MAPKK1 and MAPKK2) (Duesbery et al., 1998).

In these AB-type toxins, PA is the receptor-binding B moiety that delivers either EF or LF, as alternative enzymic A moieties, to the cytosol of mammalian cells (Leppla, 1995). Initially, PA binds specifically, reversibly, and with high affinity ($Kd \approx 1$ nM) to a cell-surface AT receptor (ATR). After binding to the receptor, PA is cleaved by a member of the furin family of proprotein convertases, which removes a 20 kDa fragment, PA20, from the N-terminus (Klimpel et al., 1992; Novak et al., 1992). The complementary fragment, PA63, remains receptor-bound and spontaneously self-associates to form heptameric ring-shaped oligomers (Milne et al., 1994) that avidly and competitively bind EF and/or LF (Leppla, 1995) to form EF/LF-PA63 complexes. These complexes are trafficked to an acidic compartment by receptor-mediated endocytosis. In the acidic compartment, the PA63 heptamers (the "prepore") are inserted into the membrane, forming transmembrane pores (Gordon et al., 1988). Concomitantly EF and LF are translocated across the membrane to the cytosol. Consistent with the pH dependence of translocation, toxin action is inhibited by lysosomotropic agents and bafilomycin A1 (Mendard et al., 1996).

EF translocation causes a large increase in intracellular cAMP concentration (Gordon et al., 1988; Gordon et al., 1989). Increased cAMP levels cause edema, and in neutrophils, inhibit phagocytosis and oxidative burst (O'Brien et al., 1985). By protecting the bacteria from phagocytosis, edema toxin apparently aids in establishing bacterial infection and proliferation in the mammalian host.

Treatment of primary macrophages and certain macrophage cell lines with lethal toxin causes cell lysis (Friedlander, 1986). Macrophage-depleted mice are resistant to treatment with lethal toxin, suggesting that macrophages are the primary targets of lethal toxin (Hanna et al., 1993). Low doses of lethal toxin induce the production of interleukin-1 and tumor necrosis factor (Hanna et al., 1993). Thus, it has been suggested that hyperproduction of cytokines causes death of the host by inducing systemic shock. How these or other proteins lead to cytokine production and macrophage lysis remains unclear.

In the past few years considerable progress has been made toward a detailed understanding of the structure and function of PA. Crystallographic structures of PA and the PA63 heptamers have been determined (Petosa et al., 1997). The prepore undergoes a major conformational change under acidic conditions to form a 14-strand transmembrane β-barrel pore (Benson et al., 1998; Miller et al., 1999). The pore structure and the detailed mechanism by which LF and EF are translocated across membranes are under intensive investigation.

The ATR structure is heretofore unknown, but is present in all cell lines that have been tested. Studies on CHO-K1 cells had indicated that PA binds to a proteinaceous receptor that is present in about $10^4$ copies/cell (Escuyer and Collier, 1991). The paucity of knowledge about the ATR represents a major gap in the understanding of how AT acts. Identification and cloning of the ATR will provide more treatment strategies for anthrax.

A cDNA clone (Genbank Accession Number NM 032208) known as tumor endothelial marker 8 (TEM8) is known (St. Croix, 2000). TEM8 is upregulated in colorectal cancer endothelium, but heretofore the function of TEM8 was not known.

BRIEF SUMMARY OF THE INVENTION

The present application discloses structures of complete and partial anthrax toxin receptors from a mammal, namely a human. The complete anthrax toxin receptor includes an extracellular domain, a transmembrane domain, and a cytoplasmic domain that can vary in length, as is disclosed herein. It is disclosed herein that PA binds to the anthrax toxin receptor at a von Willebrand factor A (VWA) domain in the extracellular domain.

In one aspect, the invention is summarized in that an anthrax toxin receptor is a polypeptide having an amino acid sequence selected from SEQ ID NO:2, SEQ ID NO:6, SEQ ID NO: 8, SEQ ID NO:10, a PA-binding fragment of any of the foregoing, and a PA-binding variant of any of the foregoing polypeptides having conservative or non-conservative amino acid substitutions or other changes relative to the disclosed sequences. The various forms of the receptor encoded by SEQ ID NO:2, SEQ ID NO:6, SEQ ID NO: 8, and SEQ ID NO:10 apparently differ as a result of alternative splicing.

In a related aspect, the invention further relates to an isolated polynucleotide that encodes any of the above-mentioned polypeptides and their complements, and a polynucleotide that hybridizes under moderately stringent or stringent hybridization conditions to any of the foregoing.

In still another related aspect, the invention encompasses a cloning vector and an expression vector comprising any of the foregoing polynucleotides, whether or not the polynucleotide is operably linked to an expression control sequence that does not natively promote transcription or translation of the polynucleotide.

By identifying the polypeptides and polynucleotides of the invention, the applicant enables the skilled artisan to detect and quantify mRNA and ATR protein in a sample, and to generate atr transgenic and atr knock-out animals using methods available to the art.

Further, the invention includes a host cell comprising any such vector in its interior. Also within the scope of the present invention is a host cell having a polynucleotide of the invention integrated into the host cell genome at a location that is not the native location of the polynucleotide.

In yet another aspect, the invention is a method for producing an anthrax toxin receptor polypeptide that includes the steps of transcribing a polynucleotide that encodes an anthrax toxin receptor polypeptide, operably linked to an upstream expression control sequence, to produce an mRNA for the receptor polypeptide, and translating the mRNA to produce the receptor polypeptide. This method can be performed in a host cell when the polynucleotide is operably linked to the expression control sequence in an expression vector, and wherein the expression vector is delivered into a host cell, the expression control sequence being operable in the host cell. Alternatively, at least one of the transcribing and translating steps can be performed in an in vitro system, examples of which are well known in the art and commercially available. In either case, the polypeptide can be isolated from other cellular material using readily available methods.

In still another aspect, the invention is a method for identifying an agent that can alter the effect of AT on the host cell or organism. The method includes the steps of separately exposing a plurality of putative agents in the presence of AT to a plurality of cells having on their surface at least a portion of the ATR that binds to AT or a component thereof, comparing the effect of AT on the cells in the presence and absence of the agent, and identifying at least one agent that alters an effect of AT on the cells. In a related aspect, the present invention encompasses an agent that alters binding of AT to the ATR.

The present invention also encompasses a method for reducing or preventing AT-related damage in vivo or in vitro to human or non-human cells having an ATR on an outer cell surface, the method comprising the step of exposing the cells to an agent that reduces binding of AT to the ATR. Similarly, the invention relates to a method for reducing or preventing damage in vivo or in vitro to human or non-human cells caused by AT by exposing AT to an agent that reduces binding of the AT to the ATR.

The present invention is also a method for identifying a mutant of the extracellular ATR domain or fragment thereof having altered (increased or reduced) binding affinity for AT.

It is an object of the invention to identify polypeptides that encode a mammalian anthrax toxin receptor, as well as fragments, mutants, and variants thereof and polynucleotides encoding same.

It is a feature of the invention that a soluble PA-binding polypeptide can reduce or eliminate toxicity associated with anthrax toxin.

Other objects, advantages and features of the invention will become apparent from the following specifications and claims.

DETAILED DESCRIPTION OF THE INVENTION

Figure 1:
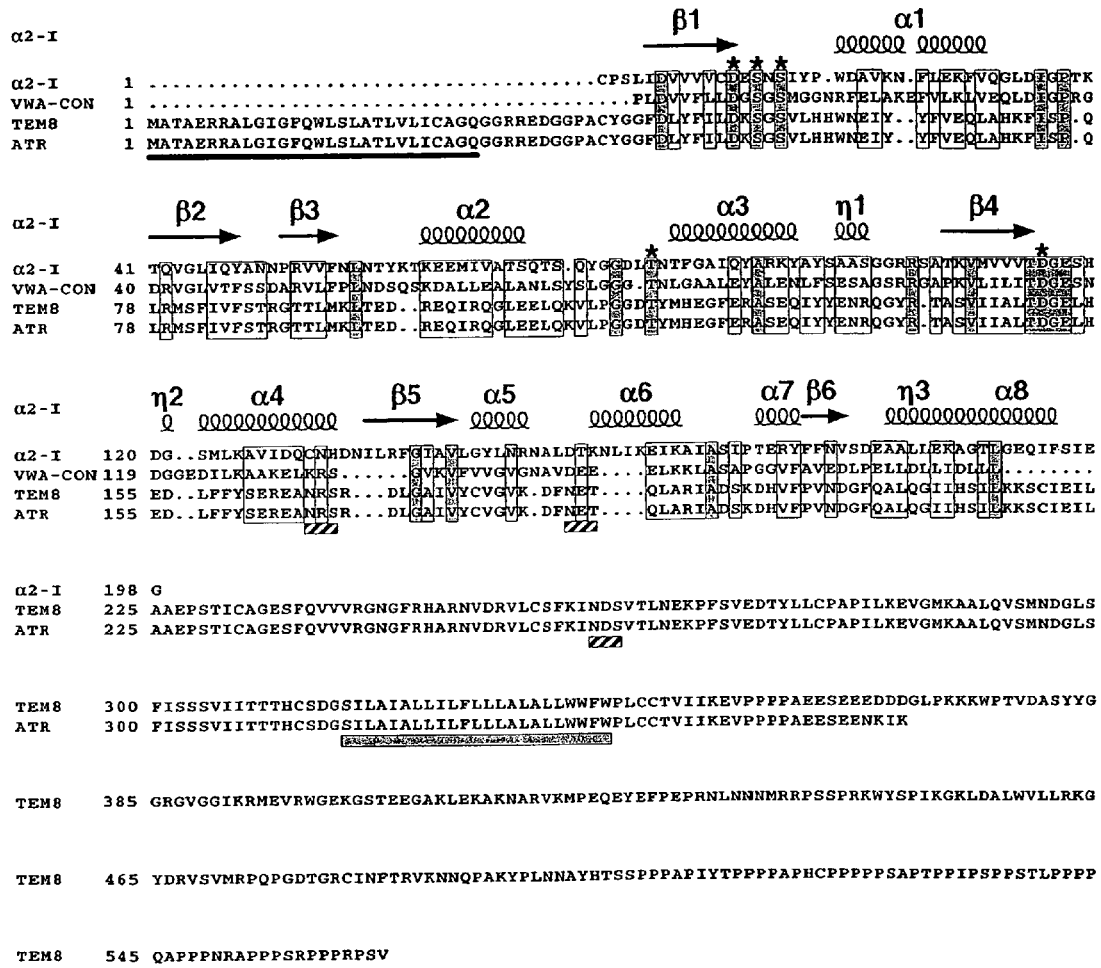
FIG. 1 shows sequence alignment of various ATR polypeptide sequences with the I domain of integrin $\alpha 2$ and with the von Willebrand factor A domain consensus sequence.

An isolated polynucleotide and an isolated polypeptide, as used herein, can be isolated from its natural environment or can be synthesized. Complete purification is not required in either case. Amino acid and nucleotide sequences flanking an isolated polypeptide or polynucleotide that occurs in nature, respectively, can but need not be absent from the isolated form.

Further, an isolated polynucleotide has a structure that is not identical to that of any naturally occurring nucleic acid or to that of any fragment of a naturally occurring genomic nucleic acid spanning more than three separate genes. The term includes, without limitation, (a) a nucleic acid molecule having a sequence of a naturally occurring genomic or extrachromosomal nucleic acid molecule but which is not flanked by the coding sequences that flank the sequence in its natural position; (b) a nucleic acid molecule incorporated into a vector or into a prokaryote or eukaryote genome such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of clones, e.g., as these occur in a DNA library such as a cDNA or genomic DNA library. An isolated nucleic acid molecule can be modified or unmodified DNA or RNA, whether fully or partially single-stranded or double-stranded or even triple-stranded. A nucleic acid molecule can be chemically or enzymatically modified and can include so-called non-standard bases such as inosine.

Reference herein to use of AT is understood to encompass use of an ATR-binding component thereof, especially PA.

Anthrax Toxin Receptor

The applicants have identified and determined the nucleic acid sequence (SEQ ID NO:1) of a cDNA clone that of a 368 amino acid long polypeptide (SEQ ID NO:2, ATR), and show herein that the polypeptide is a surface-bound anthrax toxin receptor (ATR) on human cells. Based on known structural analysis methods, the polypeptide is predicted to encode a 27 amino-acid-long signal peptide (amino acids 1–27 of SEQ ID NO:2), a 293 amino-acid-long extracellular domain (amino acids 28–320 of SEQ ID NO:2), a 23 amino-acid-long putative transmembrane region (amino acids 320–343 of SEQ ID NO:2), and a 25 amino acid long cytoplasmic domain (amino acids 344–368 of SEQ ID NO:2).

It is disclosed herein that Protective Antigen (PA) of anthrax toxin (AT) binds to the anthrax toxin receptor at a von Willebrand factor A (VWA) domain located in the portion from amino acid 44 to 216 in the extracellular domain of SEQ ID NO:2. VWA domains are present in the extracellular portions of a variety of cell surface proteins, including matrilins and integrins (designated as I domains). A VWA domain consensus sequence, VWA-CON, developed by comparing 210 related sequences, is presented as SEQ ID NO:3. These domains are important for protein/protein interactions and constitute ligand binding sites for integrins (Dickeson, 1998). The I domain of integrin α2 (α2) is presented as SEQ ID NO:4. Ligand binding through I domains requires an intact metal ion-dependent adhesion site (MIDAS) motif (Lee, 1995) which appears to be conserved in the ATR extracellular domain, as is detailed below.

Comparison of SEQ ID NO:1 and SEQ ID NO:2 to existing databases revealed other versions of those sequences. Human cDNA TEM8 (SEQ ID NO:5; Genbank accession number NM 032208) encodes a 564 amino-acid-long form (SEQ ID NO:6) of the human ATR. SEQ ID NO:6 has not previously been identified as an anthrax toxin receptor, and indeed no function has yet been ascribed to the protein. Like SEQ ID NO:1, SEQ ID NO:5 was a PCR amplification product from HeLa cells and human placenta cDNA libraries. Whereas the cytoplasmic tail of SEQ ID NO:2 is only 25 amino acids long, that of SEQ ID NO:6 is predicted to be 221 amino acids long (amino acids 344–564), presumably as a result of differential splicing of a primary mRNA transcript. The proteins are otherwise identical. Upstream of the coding sequences, SEQ ID NO:1 and SEQ ID NO:5 are also identical.

Also presented are IMAGE CLONE 4563020 (SEQ ID NO:7; Genbank Accession Number BC012074) and the predicted polypeptide encoded by the clone (SEQ ID NO:8). SEQ ID NO:8 is identical to amino acids 1–317 of ATR, but differs thereafter at the C-terminus. Similarly, human cDNA FLJ10601, clone NT2RP2005000 (SEQ ID NO:9; Genbank Accession Number AK001463) and the predicted polypeptide encoded by the clone (SEQ ID NO:10) are presented. This polypeptide is identical to a portion of SEQ ID NO:2 from amino acid 80 to amino acid 218. As with TEM8 and the protein it encodes, no function is known for any of these polynucleotide and polypeptide sequences, nor has there been any prior indication that the polypeptides are complete or partial anthrax toxin receptors.

It is of interest to note that the product of the mouse homolog of ATR/TEM8 (Genbank accession number AK013005) is highly related to the human clones, sharing greater than 98% amino acid sequence identity within the reported extracellular domain. This suggests that the anthrax toxin receptor is conserved among species. Furthermore, consistent with the observation that the anthrax toxin receptor is found in a variety of cell lines, ATR is expressed in a number of different tissues including CNS, heart, lung, and lymphocytes.

In addition to the full-length and partial ATR polypeptide sequences presented in SEQ ID NO:2, SEQ ID NO:6, SEQ ID NO:8 and SEQ ID NO:10, other polypeptide fragments shorter than those sequences that retain PA-binding activity, and variants thereof are also within the scope of the invention. The entire receptor is not required for utility; rather, fragments that bind to PA are useful in the invention.

A skilled artisan can readily assess whether a fragment binds to PA. A polypeptide is considered to bind to PA if the equilibrium dissociation constant of the binary complex is 10 micromolar or less. PA-binding to the ATR (or a fragment of the ATR) can be measured using a protein—protein binding method such as coimmunoprecipitation, affinity column analysis, ELISA analysis, flow cytometry or fluorescence resonance energy transfer (FRET), and surface plasmon resonance (SPR). SPR is particularly suited as it is highly sensitive and accurate, operable in real time, and consumes only minute amounts of protein. SPR uses changes in refractive index to quantify macromolecular binding and dissociation to a ligand covalently tethered to a thin gold chip in a micro flow cell. Besides the equilibrium dissociation constant (Kd), on- and off-rate constants (ka and kd) can also be obtained. A BIAcore 2000 instrument (Pharmacia Biotech) can be used for these measurements. Typically, a protein is covalently tethered to a carboxymethyl dextran matrix bonded to the gold chip. Binding of a proteinaceous ligand to the immobilized protein results in a quantifiable change in refractive index of the dextran/protein layer. SPR can also be used to determine whether the interaction between PA and its receptor is sensitive to low pH, which is relevant to toxin endocytosis. This technique has been used to study protein—protein interactions in many systems, including the interactions of PA63 with EF and LF (Elliott, 1998).

The invention also relates to polypeptides that are at least 80%, preferably at least 90%, more preferably at least 95%, still more preferably at least 97%, or most preferably at least 99% identical to any aforementioned PA-binding polypeptide fragment, where PA-binding is maintained. As used herein, "percent identity" between amino acid or nucleic acid sequences is synonymous with "percent homology," which can be determined using the algorithm of Karlin and Altschul (Proc. Natl. Acad. Sci. USA 87:2264–2268, 1990), modified by Karlin and Altschul (Proc. Natl. Acad. Sci. USA 90:5873–5877, 1993). Such an algorithm is incorporated into the NBLAST and XBLAST programs of Altschul et al. (J. Mol. Biol. 215:403–410, 1990). BLAST nucleotide searches are performed with the NBLAST program, score=100, wordlength=12, to obtain nucleotide sequences homologous to a nucleic acid molecule of the invention. BLAST protein searches are performed with the XBLAST program, score=50, wordlength=3, to obtain amino acid sequences homologous to a reference polypeptide (e.g., SEQ ID NO:2). To obtain gapped alignments for comparison purposes, Gapped BLAST is utilized as described in Altschul et al. (Nucleic Acids Res. 25:3389–3402, 1997). When utilizing BLAST and Gapped BLAST programs, the default parameters of the respective programs (e.g., XBLAST and NBLAST) are used. The referenced programs are available on line from the National Center for Biotechnology Information, National Library of Medicine, National Institute of Health. A variant can also include, e.g., an internal deletion or insertion, a conservative or non-conservative substitution, or a combination of these variations from the sequence presented.

Soluble fragments are of great interest as these can competitively inhibit anthrax toxin binding to the ATR and thereby can protect cells from AT intoxication in vivo and in vitro. A fragment is soluble if it is not membrane-bound and is soluble in an aqueous fluid. The extracellular ATR domain is a soluble fragment of the ATR, as are fragments of that domain. Even though the VWA domain is formally identified as extending from amino acid 44 to 216 in the extracellular domain, more or fewer natively adjacent amino acids can be included in the fragment without compromising solubility or PA-binding. For example, a PA-binding fragment having the sequence of SEQ ID NO:2 beginning at any amino acid in the range from 27 to 43 and ending at any amino acid in the range from 221 to 321. A preferred soluble, PA-binding fragment extends from amino acid 42 to 222. Another preferred soluble PA-binding fragment includes a fragment of the ATR from amino acid 27 through amino acid 321. Likewise, any polypeptide fragment of these preferred fragments that retains PA-binding activity is within the scope of the invention. ATR in soluble form is effective in a monomeric form, as well as in multimeric forms such as dimeric, tetrameric, pentameric and higher oligomeric forms.

PA-binding polypeptides can include, therefore, SEQ ID NO:2, SEQ ID NO:6, SEQ ID NO:8, SEQ ID NO:10, a PA-binding fragment of SEQ ID NO:2, a PA-binding fragment of SEQ ID NO:6, a PA-binding fragment of SEQ ID NO:8, a PA-binding fragment of SEQ ID NO:10, a PA-binding polypeptide at least 80% identical to any of the foregoing fragments. The PA-binding polypeptides can also be provided as fusion proteins comprising any of the foregoing that can comprise still other non-natively adjacent amino acids for detecting, visualizing, isolating, or stabilizing the polypeptide. For example, PA binds to a soluble fusion protein of a hexahistidine tag, a T7 tag, and amino acids 41–227 of ATR.

Likewise, isolated polynucleotides having an uninterrupted nucleic acid sequence that encodes the aforementioned polypeptides and polypeptide fragments are also useful in the invention. The sequences that encode soluble, PA-binding polypeptide fragments of ATR are immediately apparent to the skilled artisan from the description of the relevant portions of the polypeptides, supra. An isolated nucleic acid containing the complement of any such polynucleotide is also within the scope of the present invention, as are polynucleotide and oligonucleotide fragments for use as molecular probes. The polynucleotides of the invention cannot encode SEQ ID NO:6, SEQ ID NO:8 or SEQ ID NO:10.

The present invention also relates to an isolated polynucleotide and its complement, without regard to source, where the polynucleotide hybridizes under stringent or moderately stringent hybridization conditions to SEQ ID NO:1, SEQ ID NO:5, SEQ ID 7, or SEQ ID NO:9 or to a fragment of any of the foregoing that encodes a soluble polypeptide that can bind to PA. As used herein, stringent conditions involve hybridizing at 68° C. in 5×SSC/5× Denhardt's solution/1.0% SDS, and washing in 0.2×SSC/0.1% SDS+/− 100 μg/ml denatured salmon sperm DNA, at room temperature. Moderately stringent conditions include washing in the same buffer at 42° C. Additional guidance regarding such conditions is readily available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10.

In a related aspect, any polynucleotide of the invention can be provided in a vector in a manner known to those skilled in the art. The vector can be a cloning vector or an expression vector. In an expression vector, the polypeptide-encoding polynucleotide is under the transcriptional control of one or more non-native expression control sequences, such as a promoter not natively adjacent to the polynucleotide, such that the encoded polypeptide can be produced when the vector is delivered into a compatible host cell that supports expression of an polypeptide encoded on a vector, for example by electroporation or transfection, or transcribed and translated in a cell-free transcription and translation system. Such cell-based and cell-free systems are well known to the skilled artisan. Cells comprising an insert-containing vector of the invention are themselves within the scope of the present invention, without regard to whether the vector is extrachromosomal or integrated in the genome.

A skilled artisan in possession of the polypeptides and polynucleotides of the invention can also identify agents that can reduce or prevent the effect of AT on a host having on the cell surface at least a portion of the ATR. The effect altered can relate, for example, to (1) susceptibility of the host cell to AT damage, (2) integration of ATR into the cell membrane, (3) binding between ATR and PA, (4) PA heptamerization, (5) uptake of PA and ATR complex into cells, and (6) the translocation of toxin into host cell cytoplasm. The method includes separately exposing a plurality of putative agents in the presence of AT to a plurality of cells, comparing the effect of AT on the cells in the presence and absence of the agent, and identifying at least one agent that alters an effect of AT on the cells.

The skilled artisan can readily evaluate the typical effects of AT and can observe variations in those effects in the presence of a putative altering agent. For example, susceptibility to AT damage can be evaluated by exposing host cells to AT. Integration of newly formed ATR into the host cell membrane can be evaluated by labeling newly synthesized proteins in the host cell and immunopreticipating ATR from the cellular membrane fraction of the host cell. Binding of wild-type ATR to PA can be evaluated with fluorescent labeled anti-PA antibody. PA heptamerization can be evaluated by several techniques including native polyacrylamide gel electrophoresis, gel filtration, and western blotting. Uptake of PA-ATR complex can be evaluated by binding PA to ATR at 4° C., increasing the temperature to 37° C. to allow endocytosis, shifting the temperature back to 4° C., and incubating cells with fluorescent labeled anti-PA antibodies. Toxin translocation into the host cell cytoplasm can be evaluated as described in Wesche et al, 1998, which is incorporated herein by reference as if set forth in its entirety.

The agents screened can be, for example, dominant negative mutant ATRs (encoded by a mutant polynucleotide sequence, which can be provided in an expression vector), a high molecular weight molecule such as a polypeptide (including, e.g., a mutant AT, a soluble ATR, a mono- or polyclonal antibody to an ATR, to PA, or to an ATR/PA complex), a polysaccharide, a lipid, a nucleic acid, a low molecular weight organic or inorganic molecule, or the like. Antibodies can be produced by administering to a non-human animal an immunogenic, PA-binding fragment of a polypeptide which can be, e.g., SEQ ID NO:2, SEQ ID NO:6, SEQ ID NO:8, SEQ ID NO:10, a polypeptide at least 80% identical to any of the foregoing and a fusion protein comprising any of the foregoing, and then obtaining the desired antibodies using known methods.

Chemical libraries for screening putative agents, including peptide libraries, are readily available to the skilled artisan. Examples include those from ASINEX (i.e. the Combined Wisdom Library of 24,000 manually synthesized organic molecules) and from CHEMBRIDGE CORPORATION (i.e. the DIVERSet™ library of 50,000 manually synthesized chemical compounds; the SCREEN-Set™ library of 24,000 manually synthesized chemical compounds; the CNS-Set™ library of 11,000 compounds; the Cherry-Pick™ library of up to 300,000 compounds) and linear library, multimeric library and cyclic library (Tecnogen (Italy)). Once an agent with desired activity is identified, a library of derivatives of that agent can be screened for better agents. Phage display is also a suitable approach for finding novel inhibitors of the interaction between PA and ATR.

Another aspect of the present invention relates to ATR ligands other than PA and methods for identifying ATR ligands. As ATR is expressed in many cell types, it likely has other natural ligands. To identify these other ligands, a polypeptide that contains an ATR VWA domain, preferably an entire extracellular domain can be provided in soluble or tethered form, e.g., in a chromatographic column. Preferably, the ectodomain of ATR can be provided as a fusion protein that also a contains rabbit IgG constant region, a GST domain or a hexahistidine tag. This fusion protein can be immobilized on a chromatographic column using known methods. A cell extract can be passed over the column. A ligand is identified when binding is observed between the ectodomain and a compound present in the cell extract. The identified ligand can be used in methods for identifying agents that alter an effect of AT, to identify an agent that selectively inhibits PA-ATR binding. It is also desirable to use the other ligands and the ATR in comparative high throughput screening methods for identifying small molecules that do not interfere with natural ligand binding to ATR, but which do prevent or reduce binding of ATR to anthrax toxin.

The present invention also relates to reducing cellular damage caused by AT, which can be achieved by administering an agent for reducing the ATR level, inhibiting the binding between ATR and AT, or by reducing downstream ATR activity after AT binding. For example, an antisense oligonucleotide can reduce or prevent expression of atr using delivery methods known to the skilled artisan, thus reducing the cellular ATR level. An ATR-anthrax binding inhibition agent can inhibit the binding between ATR and AT. Dominant negative ATRs can block downstream ATR activities required for AT toxicity. The agents used for reducing AT damage to cells can be administered to a human or non-human animal, preferably in a standard pharmaceutical carrier, in an amount effective to reduce or eliminate anthrax toxicity.

A 20–25mer antisense oligonucleotide can be directed against 5' end of the atr message with phosphorothioate derivatives on the last three base pairs on the 3' end and the 5' end to enhance the half life and stability of the oligonucleotides. A carrier for an antisense oligonucleotide can be used. An example of a suitable carrier is cationic liposomes. For example, an oligonucleotide can be mixed with cationic liposomes prepared by mixing 1-alpha dioleylphatidylceltnanolamine with dimethldioctadecylammonium bromide in a ratio of 5:2 in 1 ml of chloroform. The solvent will be evaporated and the lipids resuspended by sonication in 10 ml of saline. Another way to use an antisense oligonucleotide is to engineer it into a vector so that the vector can produce an antisense cRNA that blocks the translation of the mRNAs encoding for ATR. Similarly, RNAi techniques, which are now being applied to mammalian systems, are also suited for inhibiting ATR expression (see Zamore, *Nat. Struct. Biol.* 8:746:750 (2001), incorporated herein by reference as if set forth in its entirety).

The present invention also relates to a method for detecting atr mRNA or ATR protein in a sample. Such detection can be readily accomplished by using oligonucleotide or polynucleotide probes for atr mRNA, or antibodies for ATR protein. In a related aspect, the antibodies made and identified as being able to bind to ATR can also be used to separate ATR from a sample.

The present invention also relates to a cell line that does not contain ATR from a parent cell line that contains ATR, and methods for making same. The present invention provides that it is possible for cells lacking ATR to survive. In the example described below, a cell line that does not contain ATR was created using mutagenesis and screening. Now that the atr cDNA sequence is identified in the present invention, many other methods for generating a cell line that does not express atr become feasible, such as homologous recombination. In addition to these methods, the cell lines generated, including the one described in the example below, are themselves within the scope of the present invention.

The invention also provides molecules and methods for specifically targeting and killing cells of interest by delivering, e.g., AT or LF to the cell. Soluble ATR molecules can be coupled to a ligand or to a single chain antibody selected for targeting to the cell of interest (e.g., a ligand that binds a receptor presented on a tumor cell surface). The coupling is most readily accomplished by producing a fusion protein that encodes both the ATR binding portion and the ligand or single chain antibody molecule. The ligand or single chain antibody domains simply serve to attach the toxin to cells with the cognate surface markers. The toxin or factor is preloaded onto the ATR portion before exposing the coupled molecules to the targeted cells. This is similar in principle to the previously described for retroviral targeting using soluble retroviral receptor-ligand bridge proteins and retroviral receptor-single chain antibody bridge proteins. See Snitkovsky and Young, *Proc. Natl. Acad. Sci. USA* 95:7063–7068 (1998); Boerger et al. *Proc. Natl. Acad. Sci. USA* 96:9687–9872 (1999) and Snitkovsky et al., *J. Virol.* 74:9540–9545 (2000), and Snitkovsky et al., *J. Virol.* 75:1571–1575 (2001), each incorporated herein by reference as if set forth in its entirety.

The invention will be more fully understood upon consideration of the following non-limiting examples.

EXAMPLES

Methods

Mutagenesis and Characterization of CHO-K1 Cells

A mutant cell line lacking the receptor was generated, so that this defect could be genetically complemented. About $5 \times 10^7$ cells of the hypodiploid CHO-K1 cell line were treated at 37° C. for 7 hr with medium containing 10 µg/ml ICR-191 (Sigma), a DNA alkylating agent that induces small deletions and frameshift mutations in genes, then washed twice. This treatment led to approximately 90% cell death.

The surviving mutagenized cells were then challenged with 8 µg/ml PA and 10 ng/ml $LF_N$-DTA, a fusion protein composed of the N-terminal 255 amino acids of LF linked to the catalytic A chain of diphtheria toxin. This recombinant toxin can kill CHO-K1 cells (in contrast to LF and PA) and it exploits the same LF/PA/receptor interactions that are required for the binding and entry of the native LF and EF proteins. After 4 days, surviving cells were replated and incubated for 3 days with medium containing PA and $LF_N$-DTA. Ten single-cell colonies (designated as CHO-R1.1 to CHO-R1.10) that survived toxin treatment were isolated 14 days later. In control experiments performed with non-mutagenized CHO-K1 cells, no toxin-resistant cell clones were detected.

One of the mutagenized clones (CHO-R1.1) was chosen for further analysis. CHO-R1.1 cells were found to be fully susceptible to killing by diphtheria toxin (DT) by measuring $^3$H-leucine incorporation into cellular proteins after exposure to the toxin, thus ruling out the possibility that resistance to PA/$LF_N$-DTA was due to a defect in the pathway of DT action. To test directly whether CHO-R1.1 cells lacked the receptor, flow cytometric analysis was performed after the cells were incubated at 4° C. for 2 hr in medium containing 40 to 80 nM PA-K563C coupled at mutated residue 563 to Oregon Green maleimide (Molecular Probes) ("OGPA"). The treated cells were washed twice with medium and analysed using a Becton Dickinson FACSCalibur flow cytometer. CHO-R1.1 cells were significantly impaired in their ability to bind to OGPA as compared to the parental cell line, suggesting that these mutagenized cells had lost expression of the putative PA receptor gene. Similar analysis of the other nine mutant CHO-R1 clones demonstrated that they were also defective in binding to OGPA.

cDNA Complementation

In an attempt to complement the PA binding defect of CHO-R1.1 cells, the cells were transduced with a retrovirus-based cDNA library (Clontech) prepared from human HeLa cells that express the PA receptor. This cDNA library is contained in a murine leukemia virus (MLV) vector that is packaged into pseudotyped virus particles (MLV[VSV-G]) containing the broad host-range G protein of vesicular stomatitis virus (VSV-G). Retrovirus-based cDNA libraries are useful for genetic complementation approaches since they can deliver a limited number of stably expressed cDNA molecules per cell. These molecules can be rapidly re-isolated by PCR amplification using MLV vector-specific oligonucleotide primers.

Approximately $5 \times 10^5$ CHO-R1.1 cells were transduced with about $10^7$ infectious units (complexity of library=$2 \times 10^6$ independent clones) of the pLIB-based cDNA library (Clontech; cat.# HL8002BB) produced in the 293GPG packaging cell line. Three days later, cells were incubated with medium containing 80 nM OGPA and the top 0.1% of fluorescent cells were then isolated by sorting using a Becton Dickinson FACSVantageSE instrument. Cells were sorted based on their binding of OGPA in combination with an anti-PA polyclonal serum and an allophycocyanin (APC) conjugated secondary antibody. To isolate those that contained the putative PA receptor cDNA clone, these cells were expanded and subjected to four additional rounds of sorting using OGPA as above, as well as a 1:500 dilution of a rabbit anti-PA polyclonal serum along with a 1:500 dilution of an APC-conjugated secondary antibody (Molecular probes). OGPA-single positive (round 2) or OGPA/APC-double positive (rounds 3–5) cells were recovered (the top 20%, 1%, 5%, and 50% of fluorescent cells for rounds 2, 3, 4, and 5 respectively) and expanded after each round of sorting.

This led to the isolation of a cell population in which greater than 90% of the cells bound OGPA. This complemented cell population contained at least seven unique cDNA inserts that were obtained by the PCR amplification method described above. Each cDNA was gel purified, subcloned back into the parent pLIB vector and packaged into MLV(VSV-G) virions so that it could be tested for its ability to complement the PA-binding defect of CHO-R1.1 cells. One cDNA clone of approximately 1.5 kb (designated as ATR) restored PA binding to CHO-R1.1 cells. This clone also dramatically enhanced the binding of PA to parental CHO-K1 cells.

Furthermore, the ATR cDNA clone fully restored $LF_N$-DTA/PA toxin sensitivity to CHO-R1.1 cells. In this test, CHO-R1.1 cells and CHO-K1 cells were either not transduced or transduced with the MLV vector encoding ATR; these cells were treated with $10^{-9}$ M $LF_N$-DTA and various concentrations of PA; medium containing 1 µCi/mL $^3$H-leucine was then added to cells for 1 hr, and the amount of $^3$H-leucine incorporated into cellular proteins was determined by trichloroacetic acid precipitation and liquid scintillation counting.

cDNA Characterization cDNA inserts were recovered from these cells by PCR amplification of genomic DNA samples using oligonucleotide primers specific for the MLV vector according to the manufacturers instructions (Clontech). Each cDNA was subcloned between the NotI and SalI restriction enzyme sites of pLIB and the resulting plasmids were co-transfected into 293 cells with MLV gag/pol and VSV-G expression plasmids pMD.old.gagpol and pMD.G. Resulting pseudotyped virus particles were used to infect CHO-R1.1 and CHO-K1 cells followed by OGPA staining and FACS analysis as above.

Sequencing of the ATR cDNA clone revealed a single long open reading frame, encoding a 368 amino acid protein. FIG. 1 shows sequence alignment of ATR (SEQ ID NO:2) with the von Willebrand factor A domain consensus sequence (SEQ ID NO:3; VWA-CON), the I domain of integrin α2 (SEQ ID NO:4; α2), and TEM8 (SEQ ID NO:6). The secondary structural elements are based on the crystal structure of the α2 I domain. Conserved amino acids are boxed and identical amino acids are indicated by shaded boxes. The putative signal sequence is underlined. The five residues that form the MIDAS motif are indicated with asterisks. The putative transmembrane domains of ATR and TEM8 are indicated with a shaded box. Potential N-linked glycosylation sites in ATR and TEM8 are indicated by hatched boxes. The alignment was made using the programs ClustalW and ESPript 1.9.

The ATR protein is predicted to have a 27 amino acid long signal peptide, a 293 amino acid long extracellular domain with three putative N-linked glycosylation sites, a 23 amino acid long putative transmembrane region, and a short cytoplasmic tail. A BLAST search revealed that the first 364 amino acids of ATR are identical to a protein encoded by the human TEM8 cDNA clone (Genbank accession number NM 032208). The C-terminal ends of ATR and the TEM8 protein then diverge, presumably as a consequence of alternative splicing, such that ATR has a cytoplasmic tail of only 25 amino acids whereas TEM8 is predicted to have a 221 amino acid long cytoplasmic tail. The most notable feature of ATR is the presence of an extracellular von Willebrand Factor type A (VWA) domain, located between residues 44 and 216.

The cytoplasmic tail of ATR contains an acidic cluster (AC motif) (EESEE) that is similar to a motif found in the cytoplasmic tail of furin which specifies basolateral sorting of this protease in polarized epithelial cells. This may be significant because the PA receptor localizes to the basolateral surface of polarized epithelial cells and it is expected that the receptor and the protease needed to bind and activate PA would be co-localized to allow for efficient entry of anthrax toxins.

Cloning and Expression of T7-$ATR_{41-227}$

A fusion protein having a hexahistidine tag, a T7 tag, and amino acids 41 to 227 of ATR (the I domain) was constructed, expressed and purified from *E. coli* cells as follows. A DNA fragment encoding amino acids 41–227 of ATR was cloned into the BamH1 and EcoR1 sites of pET28A (Novagen) to generate pET28A-$ATR_{41-227}$. BL21 (DE3) cells (Stratagene) containing pET28A-$ATR_{41-227}$ were grown at 37° C. to an $OD_{600}$ of 0.6, induced with 1 mM isopropyl-β-D-thiogalactopyranoside for 4 hr and harvested by centrifugation. The cells from 1.5 L of culture were resuspended in 25 mL of 50 mM Tris-HCl pH 8.0, 2 mM dithiothreitol (DTT), 1 mM phenylmethylsulfonyl fluoride and were passed through a French press. One milligram of DNAse I (Roche) was added to the cell lysate, which was then sonicated for 1 min and centrifuged at 21,000 g for 20 min. The pellet was resuspended in 25 mL of 50 mM Tris-HCl pH 8.0, 2 mM DTT and centrifuged at 21,000 g for 20 min. This wash step was repeated once. T7-ATR$_{41-227}$ was solubilized and folded essentially as described previously.

When mixed with wild-type PA (on ice for 30 min), this construct was precipitated with polyclonal anti-PA serum (analyzed by SDS-PAGE and Western blot using anti-T7 antibody conjugated to horseradish peroxidase). The interaction between PA and T7-ATR$_{41-227}$ was impaired by the presence of EDTA (2 mM), demonstrating that the involvement of divalent cations in the interaction, and suggesting that the ATR MIDAS motif is involved in binding PA.

Interaction Between PA and ATR

PA-N682S, a mutant form of PA isolated as described below and having an impaired ability to bind and intoxicate cells, did not bind to T7-ATR$_{41-227}$. The DNA encoding Domain 4 of PA was mutagenized using error-prone PCR. Clones were expressed in E. coli, and lysates derived from these clones were added to CHO-K1 cells in combination with LF$_N$-DTA. Clones corresponding to lysates that did not kill CHO-K1 cells were sequenced and the N682S mutant clone was further characterized as having Ser in place of Asn at position 682.

PA-N682S was shown to have an impaired ability to bind cells as follows. CHO-K1 cells were incubated with 2×10$^8$ M trypsin-nicked PA (wild-type or N682S) for 1 hr, washed with PBS, resuspended in SDS sample buffer and run on a 4–20% polyacrylamide SDS gel, and PA was visualized by Western blotting. In the experiment in which PA-N682S was shown to have an impaired ability to intoxicate cells, CHO-K1 cells were incubated with LF$_N$-DTA (10$^{-9}$ M) and various concentrations of wild-type PA or PA-N682S mutant, and cell viability was determined.

To confirm that PA binds directly to ATR, co-immunoprecipitations (using a polyclonal serum specific for PA and protein A agarose) were performed with an extracellular fragment of ATR and either the wild-type or a receptor binding-deficient mutant form of PA. A mixture of 5 µg PA (WT or N682S) and 2 µg T7-ATR$_{41-227}$ (in 20 mM Tris-HCl pH 8.0, 150 mM NaCl, 0.1 mg bovine serum albumin per mL) was incubated on ice for 30 min in the presence or absence of 2 mM EDTA. Anti-PA polyclonal serum (10 µL) was added to this solution and incubated on ice for an additional 1 hr. Protein A agarose (Santa Cruz Biotechnology) was added and the solution was rotated at 4° C. for 1 hr, then washed four times with 20 mM Tris-HCl pH 8.0, 150 mM NaCl. Approximately one third of the mixture was subjected to SDS-PAGE, transferred to nitrocellulose and probed with anti-T7 antibody conjugated to horseradish peroxidase (Novagen).

In addition, a fusion protein containing GST and the PA receptor-binding domain (D4) (GST-D4) bound T7-ATR$_{41-227}$, while GST did not. DNA encoding amino acids 595 to 735 of PA (domain 4) was cloned into pGEX-4T-1 (Pharmacia Biotechnology). This vector encoded the GST-D4 fusion protein. GST-D4 was coupled to glutathione sepharose at a concentration of 4 mg GST-D4 per mL according to manufacturer's instructions (Pharmacia Biotechnology). GST or GST-D4 coupled to glutathione sepharose was mixed with 2 µg of T7-ATR$_{41-227}$ and 250 µg of E. coli extract in a volume of 250 µL for 1 hr at 4° C. The beads were washed 4 times with 20 mM Tris-HCl pH 8.0, 150 mM NaCl. One half of the suspension was subjected to SDS-PAGE, transferred to nitrocellulose, and probed with anti-T7 antibody coupled to horseradish peroxidase.

Taken together, the experiments described above demonstrate a direct and specific interaction between the VWA/I domain of ATR and the receptor-binding domain of PA. Given this direct interaction, we reasoned that ATR$_{41-227}$ might protect CHO-K1 cells from killing by PA and LF$_N$-DTA. This idea was tested by incubating (37° C. for 4 hr) CHO-K1 cells with an increasing amount of T7-ATR$_{41-227}$ in the presence of a constant amount of PA (10$^{-10}$ M)/LF$_N$-DTA (2.5×10$^{-11}$ M), and then measuring the subsequent effect on protein synthesis. T7-ATR$_{41-227}$ was an effective inhibitor of toxin action, inhibiting toxin activity by 50% and 100% at concentrations of 80 nM and 500 nM respectively. T7-ATR$_{41-227}$ did not, however, inhibit diphtheria toxin.

The present invention is not intended to be limited to the foregoing, but encompasses all such modifications and variations as come within the scope of the appended claims.

We claim:

1. An isolated polynucleotide or complement thereof, the polynucleotide comprising a nucleotide sequence encoding the amino acid sequence of SEQ ID NO:2.

2. An isolated polynucleotide or complement thereof, the polynucleotide encoding an the amino acid sequence selected from the group consisting of SEQ ID NO:2, amino acids 27–321 of SEQ ID NO:2, and amino acids 28–320 of SEQ ID NO:2.

3. The isolated polynucleotide of claim 1 comprising SEQ ID NO:1 from position 104 to 1207 or the complement thereof.

4. An isolated polynucleotide or complement thereof, the polynucleotide encoding the amino acid sequence selected from the group consisting of amino acids 41–227 of SEQ ID NO:2, amino acids 42–222 of SEQ ID NO:2, and amino acids 44–216 of SEQ ID NO:2.

5. The isolated polynucleotide of claim 4 wherein the polynucleotide encodes an the amino acid sequence selected from the group consisting of amino acids 41–227 of SEQ ID NO:2 and amino acids 42–222 of SEQ ID NO:2.

6. A vector comprising the polynucleotide of claim 1.

7. A vector comprising a non-native expression control sequence operably linked to a polynucleotide selected from the group consisting of the polynucleotide of claim 1 and a polynucleotide of claim 4.

8. The vector of claim 7, wherein the polynucleotide is selected from the group consisting of the polynucleotide of claim 1 and a polynucleotide of claim 4.

9. A host cell comprising a non-native expression control sequence operably linked to a polynucleotide selected from the group consisting of the polynucleotide of claim 1 and a polynucleotide of claim 4.

10. The host cell of claim 9, wherein the polynucleotide is selected from the group consisting of the polynucleotide of claim 1 and a polynucleotide of claim 4.

11. A method for producing an anthrax toxin receptor, the method comprising the steps of:
transcribing a polynucleotide operably linked to an upstream expression control sequence, wherein the polynucleotide is selected from the group consisting of the polynucleotide of claim 1 and a polynucleotide of claim 4 to produce an mRNA; and
translating the mRNA to produce the anthrax toxin receptor.

12. A method as claimed in claim 11, wherein the polynucleotide is operably linked to the expression control sequence in an expression vector, and wherein the expression vector is delivered into a host cell, the expression control sequence being operable in the host cell.

13. A method as claimed in claim 11, wherein at least one of the transcribing and translating steps are performed in vitro.

14. The method of claim 11, wherein the polynucleotide is selected from the group consisting of the polynucleotide of claim 1 and a polynucleotide of claim 4.

* * * * *